United States Patent [19]

Boyd et al.

[11] Patent Number: 5,468,843
[45] Date of Patent: Nov. 21, 1995

[54] ACETIC ANHYDRIDE ACTIVATION FOR C-TERMINAL PROTEIN SEQUENCING

[75] Inventors: Victoria L. Boyd, San Carlos; MeriLisa Bozzini, Burlingame, both of Calif.; G. Marc Loudon, West Lafayette, Ind.

[73] Assignee: Perkin-Elmer, Norwalk, Conn.

[21] Appl. No.: 302,154

[22] Filed: Sep. 8, 1994

[51] Int. Cl.⁶ ............................ C07K 1/10; G01N 33/68
[52] U.S. Cl. ............................ 530/345; 436/89; 436/90; 530/408
[58] Field of Search ..................... 500/75, 408; 406/89, 406/90

[56] References Cited

U.S. PATENT DOCUMENTS

| | | | |
|---|---|---|---|
| 4,935,494 | 6/1990 | Miller | 530/345 |
| 5,041,388 | 8/1991 | Boyd et al. | 436/89 |
| 5,049,507 | 9/1991 | Hawke et al. | 436/89 |
| 5,051,368 | 9/1991 | Boyd et al. | 436/89 |
| 5,066,785 | 11/1991 | Miller | 530/345 |
| 5,180,807 | 1/1993 | Bailey et al. | 530/345 |
| 5,185,266 | 2/1993 | Boyd et al. | 436/89 |
| 5,304,497 | 4/1994 | Boyd et al. | 436/89 |

FOREIGN PATENT DOCUMENTS

| | | |
|---|---|---|
| 1-250863 | 10/1989 | Japan . |
| WO90/05739 | 5/1990 | WIPO . |
| WO91/09868 | 7/1991 | WIPO . |

OTHER PUBLICATIONS

Stark, "Sequential degradation of peptides from their carboxyl termini with ammonium thiocyanate and acetic anhydride," Biochemistry, 7: 1796–1807 (1968).
Cromwell et al, "Determination of the carboxyl termini of proteins with ammonium thiocyanate and acetic anhydride, wtih direct identification of the thiohydantoin," Biochemistry, 8: 4735–4740 (1969).
Cosmatos et al, "Peptidsynthesen uber N–phosphorylaminosaure–phosphorsaure–anhydride," Peptidsynthesen, Jahrg. 94, pp. 2644–2655 (1961).
Meuth et al, "Stepwise sequence determination from thecarboxyl terminus of peptides," Biochemistry, 21: 3750–3757 (1982).
Bailey et al, "Automated carboxy–terminal sequence analysis of peptides," Protein Science, 1: 68–80 (1992).
Inglis, "Chemical procedures for C–terminal sequencing of peptides and proteins," Anal. Biochem., 195: 183–196 (1991).
Kenner et al, "Selective removal of the C–terminal residue as a thiohydantoin. The use of diphenyl phosphorisocyanatidate," Peptides. Part IV. pp. 673–678 (1953).
Bailey and Shively, "Carboxy–terminal sequencing: formation and hydrolysis of C–terminal peptidylthiohydantoins," Biochemistry, 29: 3145–3156 (1990).
Boyd et al, "Sequencing of peptides and proteins from the carboxy terminus," Anal. Biochemistry, 206: 344–352 (1992).
Waley et al, "The stepwise degradation of peptides," J. Chem. Soc. 1951: 2394–2397.

Primary Examiner—Howard E. Schain
Attorney, Agent, or Firm—Stephen C. Macevicz

[57] ABSTRACT

A method is provided for C-terminal sequencing of a protein or peptide. An important feature of the method is the formation of an oxazolone moiety at the C-terminus of a protein or peptide by treatment with acetic anhydride under basic conditions followed by conversion of the oxazolone to a thiohydantoin moiety by treatment with thiocyanate under acidic conditions. Yields of thiohydantoin are further enhanced by delivering thiocyanate as the conjugate acid of a sterically hindered alkylammnonium cation.

18 Claims, 18 Drawing Sheets

Activate with acetic anhydride under basic conditions

Treat with t-butylammonium thiocyanate under acidic conditions

Alkylate thiohydantoin moiety

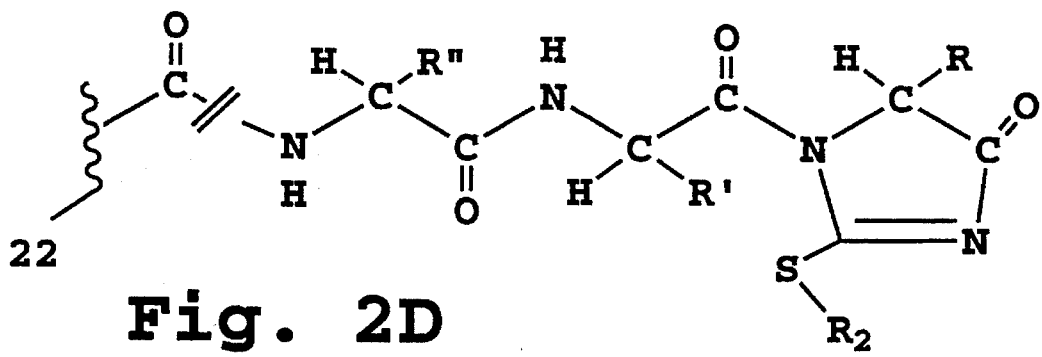
Fig. 2D
Treat with t-butylammonium thiocyanate
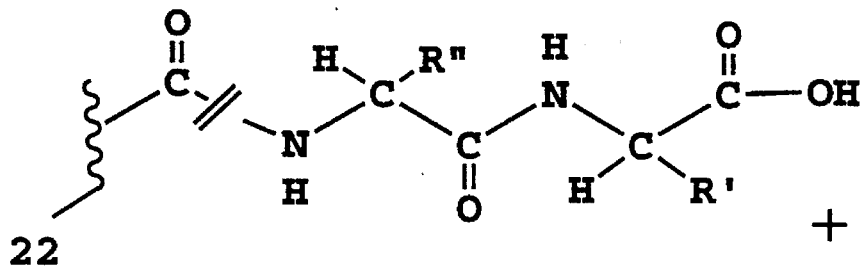
Fig. 2E
+
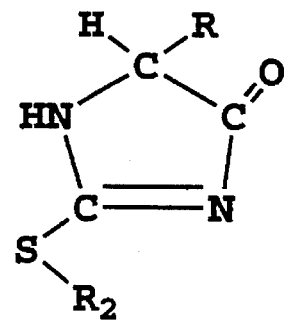

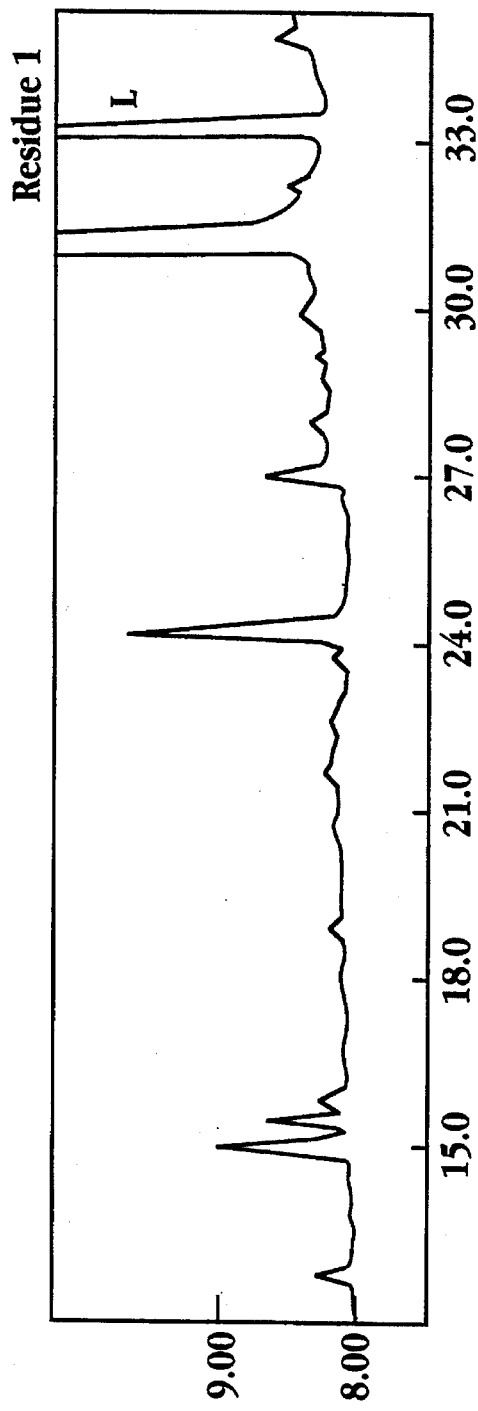
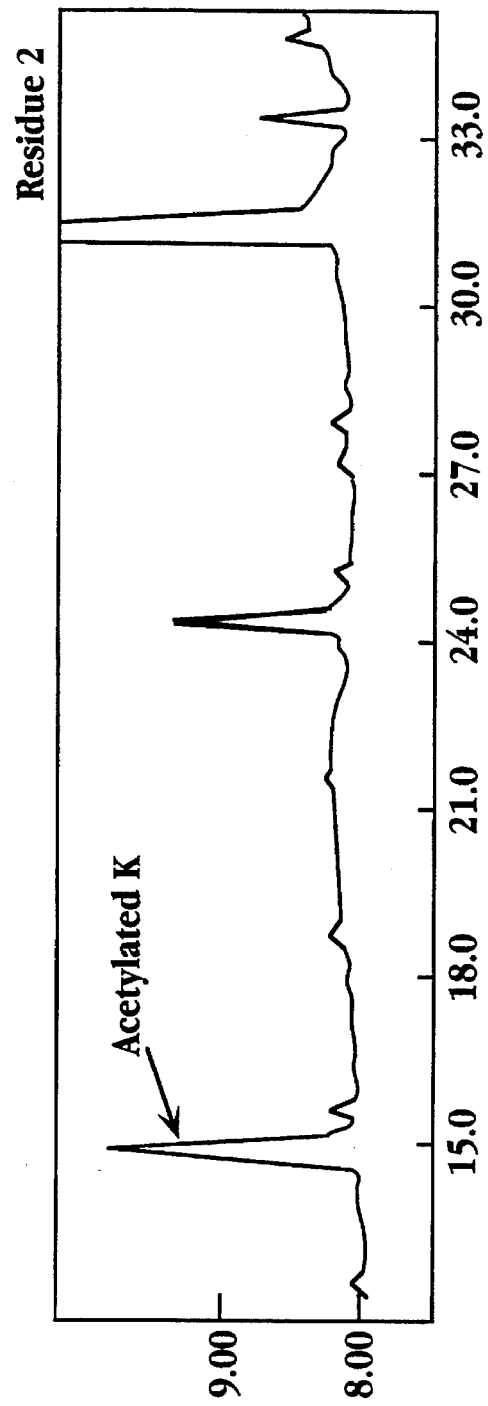
Fig. 6A
Fig. 6B

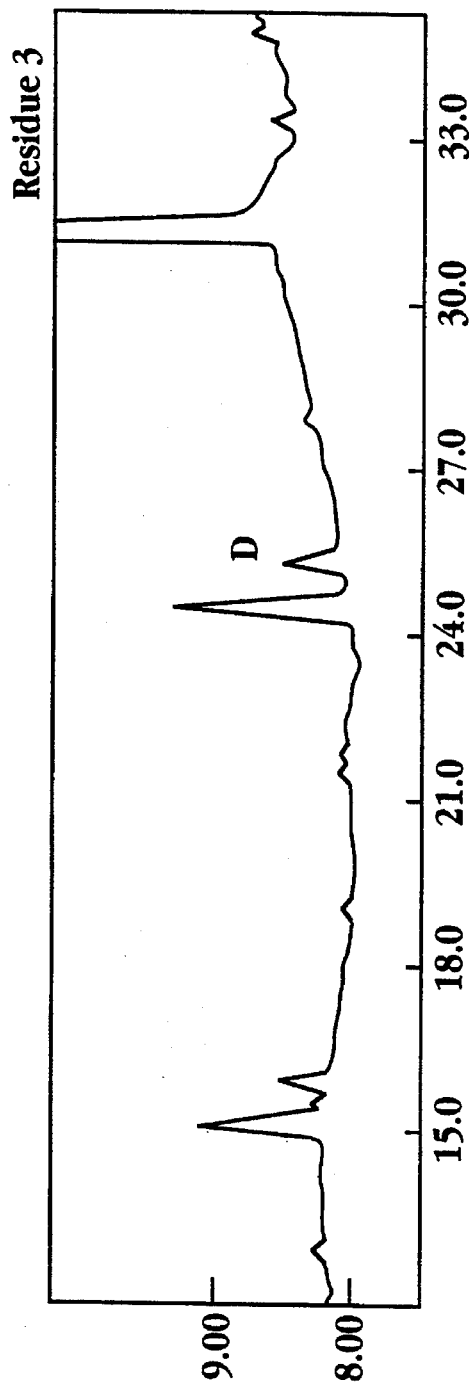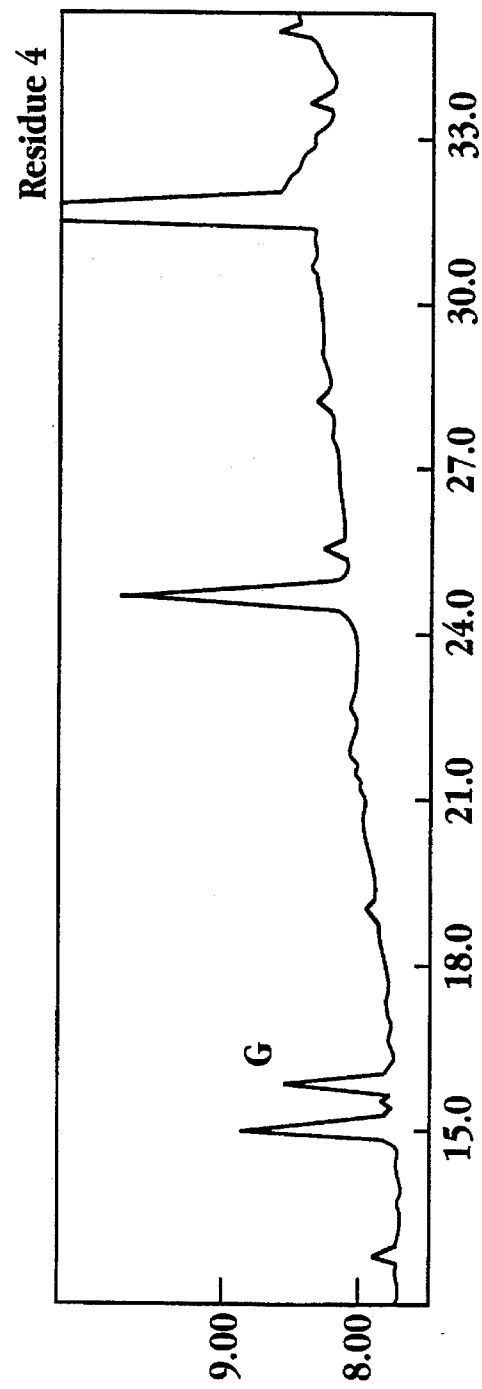

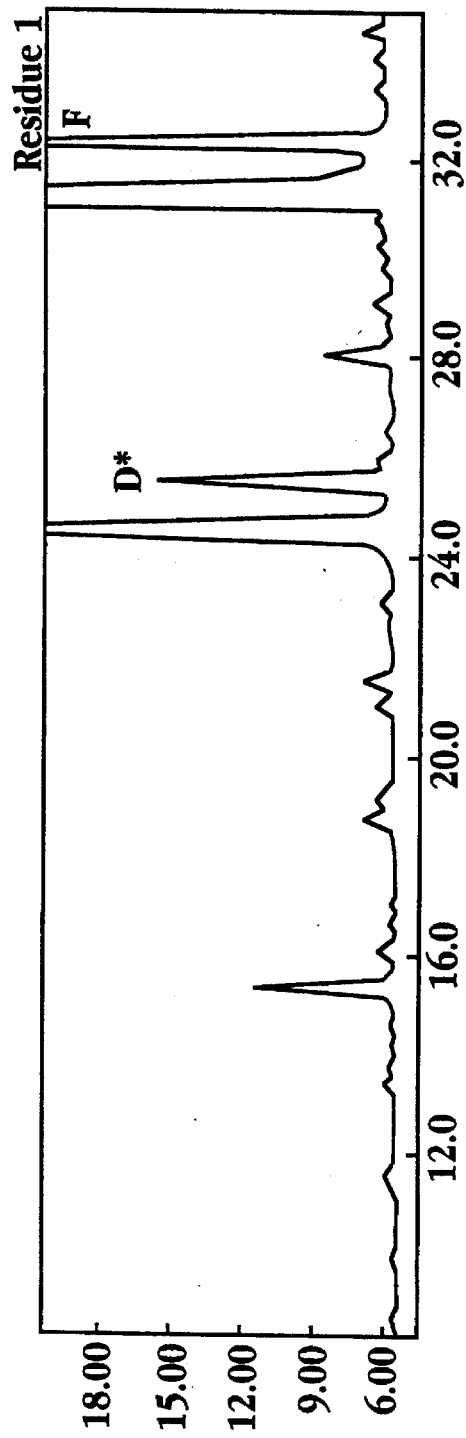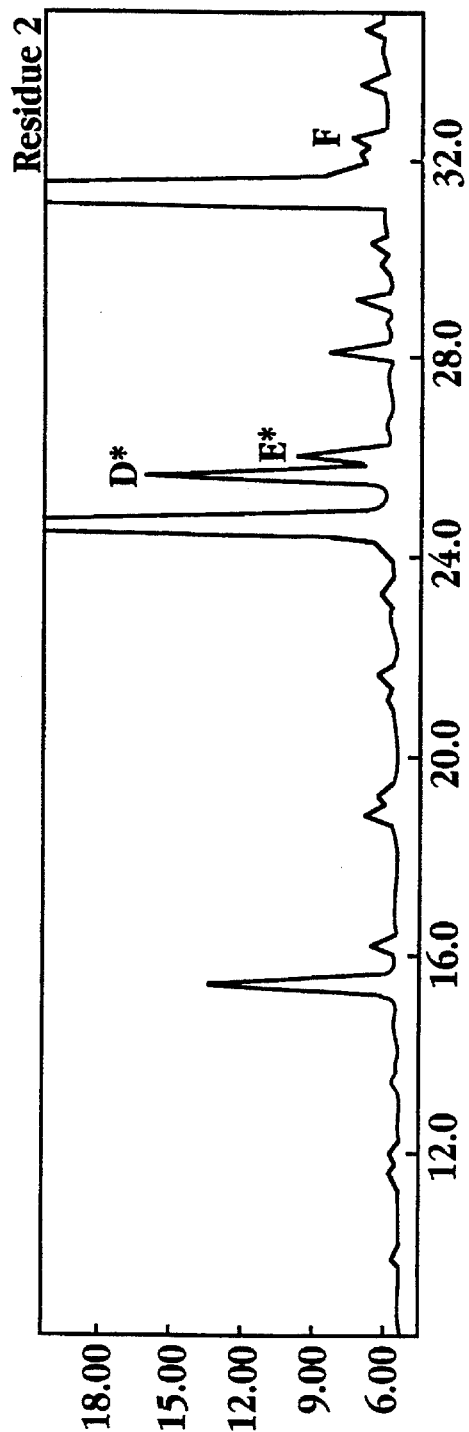

ACETIC ANHYDRIDE ACTIVATION FOR C-TERMINAL PROTEIN SEQUENCING

FIELD OF THE INVENTION

The present invention relates generally to a method of determining the amino acid sequence of the C-terminus of a peptide or protein, and more particularly, to a method of forming an amino acid thiohydantoin at the C-terminus of a peptide or protein.

BACKGROUND OF THE INVENTION

Progress in C-terminal sequencing of peptides and proteins has been slow and painstaking over the last several decades in comparison to N-terminal peptide sequencing, e.g. Inglis, Analytical Biochemistry, 195:183–196 (1991). An important approach to C-terminal sequencing involves the formation of a thiohydantoin moiety at the C-terminus of the peptide or protein sample, which is then cleaved and detected in much the same manner that a phenylthiohydantoin moiety is formed, cleaved, and detected in the Edman degradation approach to analyzing N-terminal amino acid residues.

Much of the current research into C-terminal sequencing methodologies has focused on the development of better reagents for thiohydantoin formation, e.g. Bailey et al, Biochemistry, 29:3145–3156 (1990); Boyd et al, U.S. Pat. No. 5,051,368; Bailey et al, U.S. Pat. No. 5,180,807; Boyd et al, U.S. Pat. No. 5,304,497; and the like. A variety of chemical methods have been proposed for converting the C-terminal amino acid of a peptide to its corresponding thiohydantoin (TH), e.g. Inglis (cited above). In particular, Stark and others have employed acetic anhydride under acidic conditions to activate the C-terminal residue, which is concurrently treated with thiocyanate {N=C=S}$^-$ to produce a thiohydantoin derivative, e.g. Stark, Biochemistry, 7:1796–1807 (1968). The chemical mechanism underlying such activation and thiohydantoin formation is not well understood, but it is believed to involve the formation of mixed anhydrides and oxazolones. Unfortunately, the oxazolones are thought to participate in several undesirable side reactions which tends to reduce the yield of thiohydantoin.

It would be advantageous if there were available an alternative chemistry for forming thiohydantoins in C-terminal peptide sequencing that resulted in higher thiohydantoin yields and that could thereby support a greater number of sequencing cycles on reasonably sized samples.

SUMMARY OF THE INVENTION

The present invention includes a method of selectively convening a C-terminal N-protected amino acid to a corresponding amino acid thiohydantoin. An important feature of the invention is the generation of an oxazolone moiety at a C-terminal carboxyl of a peptide or protein sample by treating the sample with acetic anhydride under mildly basic conditions. Under such conditions, the amount of oxazolone lost to undesirable side reactions is greatly reduced, thereby permitting a higher percentage of oxazolone to be converted to thiohydantoin by subsequent treatment with thiocyanate.

In another aspect, the invention includes a method of sequencing a plurality of C-terminal residues in a polypeptide or protein. Preferably, such method comprise the steps of (1) treating the C-terminal amino acid of the polypeptide with acetic anhydride under mildly basic conditions to form an oxazolone moiety, (2) treating the oxazolone moiety by a thiocyanate anion under acidic conditions to form an amino acid thiohydantoin, (3) cleaving the amino acid thiohydantoin from the polypeptide, an (4) identifying the cleaved amino acid thiohydantoin. More preferably, the method further includes the steps of (i) treating the polypeptide sample with acetic anhydride under mildly basic conditions and with piperidine thiocyanate to convert side-chain carboxyl groups to piperidine amides, (ii) treating the polypeptide sample with an acetylating agent to convert the side-chain hydroxyls of serine and threonine to O-acetyl derivatives, and (iii) treating the amino acid thiohydantoin formed in step (2) above with an alkylating agent to form an alkylated thiohydantoin.

An important aspect of the invention is the selective and efficient formation of an oxazolone moiety at the C-terminus of a polypeptide sample. This permits the C-terminal carboxylic group to be chemically distinguished from the side-chain carboxylic groups of aspartic and glutamic acids. Preferably, after oxazolone formation side-chain carboxyl groups of aspartic and glutamic acid are amidated to render them non-reactive to further steps in the sequencing process.

In another aspect, the method is used in the preparation of amino acid thiohydantoin standards, e.g., for use in C-terminal sequence analysis by HPLC.

These and other objects and features of the invention will become more fully apparent when the following detailed description of the invention is read in conjunction with the accompanying drawings.

BRIEF DESCRIPTION OF THE DRAWINGS

FIGS. 2A–2E illustrate steps in a method of C-terminal sequencing of a peptide in accordance with the invention.

FIGS. 6A–6D are chromatograms of cleaved arylalkylated amino acid thiohydantoins from the C-terminal sequencing of enolase.

FIGS. 7A–7D are chromatograms of cleaved arylalkylated amino acid thiohydantoins from the C-terminal sequencing of RecA.

Definitions

The following terms, as used herein, have the meanings as indicated:

Preferably, the term "oxazolone" usually means a radical defined by the formula:

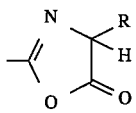

wherein R is typically an amino acid side-chain.

Figure 1A:
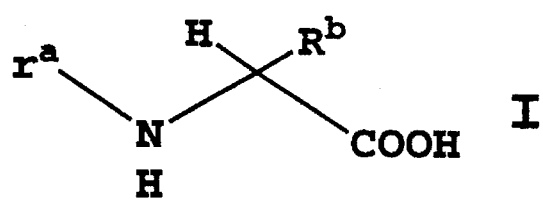
FIGS. 1A–1C illustrate the formation of a thiohydantoin moiety at the C-terminus of a peptide.

"N-protected amino acid" refers to an amino acid or a polypeptide having a protecting group bonded to its α-amino group. Typical protecting groups include Fmoc, Boc, acyl, polypeptidyl, and amine-reactive groups bound to a solid support, as are well-known in the art. A structural formula for an N-protected amino acid is shown in FIG. 1A, where $R^a$ represents the protecting group. The amino acid, whose side chain is represented by $R^b$, may have additional protecting groups to mask an amine, carboxylate, sulfhydryl, or hydroxyl group in the side chain. Such side-chain groups are sometimes referred to herein as "side-chain carboxyl groups," "side-chain sulfhydryl groups," and "side-chain hydroxyl groups," respectively, of a peptide, polypeptide, or protein.

"Peptide" and "polypeptide" refer to a peptide containing two or more amino acid residues, including a native or denatured protein. In FIG. 1A, the protected amino acid is the C-terminal residue of a peptide if the protecting group ($R^a$) includes one or more amino acid residues coupled to the C-terminal residue via an amide bond. As used herein, the term "polypeptide" encompasses terms "peptide," "polypeptide," and "protein."

Figure 1B:
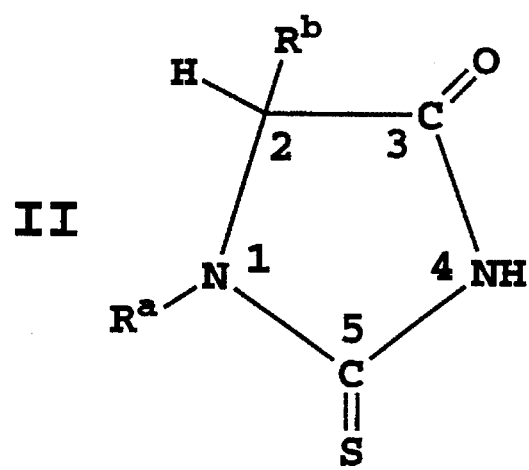
Figure 1C:
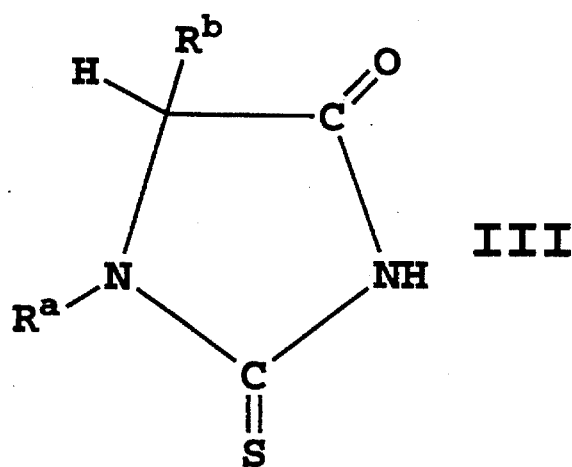

"Amino acid thiohydantoin" or "amino acid TH" refers to members of the class of compounds having the structural formula shown in FIG. 1B, where $R^b$ is an associated side chain of an amino acid, and the numerals 1 to 5 indicate the conventional numbering scheme for the thiohydantoin. In accordance with the present invention, a thiohydantoin is formed from an N-protected amino acid, which may include an N-protected free amino acid or the C-terminal amino acid of a peptide. As used herein, an amino acid TH can have an N-protecting group, as shown at II in FIG. 1B, or can be deprotected, i.e., released from or lacking an N-protecting group, as shown in FIG. 1C.

"N-protected peptidyl thiohydantoin" and "C-terminal peptidyl thiohydantoin" refer to an N-protected thiohydantoin in which the protecting group is a polypeptide.

"Isothiocyanate reagent" or "thiocyanate reagent" refers to a chemical species that can provide a thiocyanate [SCN]⁻ anion.

"Solid support" or "solid phase support" refers to any solid support that has surface functionality or can be derivatized to have surface functionality. Preferably, the surface functionality can interact with an amino group of a peptide so as to bind the peptide to the support. Such binding can be by covalent linkage, ionic interactions, and/or hydrophobic interactions. Exemplary solid supports include, but are not limited to, Sepharose™, an aminopropyl derivative of silica, aminopropyl-CPG (controlled pore glass), aminoethyl cellulose, Tris-aryl$^R$-NH, glass beads, polyacrylamide particles, 1,4-phenylene diisothiocyanate (DITC) glass, functionalized polystyrene, polyethylene, membrane supports such as functionalized PVDF, and the like.

"In the C-terminal region of a polypeptide" refers to a residue which is located in a polypeptide near the C-terminus of the polypeptide (within 50 residues of the C-terminal residue).

DETAILED DESCRIPTION OF THE INVENTION

In accordance with the invention, an N-protected amino acid, preferably at the C-terminus of a protein or peptide, is reacted with acetic anhydride or a homolog thereof in the presence of a mild base to form a 2-alkyl-5(4H)-oxazolone. The oxazolone is then reacted with a thiocyanate under acidic conditions to form the corresponding N-protected amino acid thiohydantoin. Preferably, thiocyanate is provided as a salt of a hindered alkylamine which is weakly nucleophilic, or even more preferably, non-nucleophilic in comparison to the thiocyanate. The absence of nucleophilicity in the conjugate is preferred so that undesirable side products are not generated by nucleophilic attack by the conjugate on the oxazolone moiety in competition with the thiocyanate. Preferably, the mild base used with the acetic anhydride or homolog is also non-nucleophilic relative to the oxazolone and has a $K_b$ in the range of between about $10^{-7}$ to about $10^{-12}$. More preferably, the mild base is an aromatic amine containing from 1 to 4 nitrogen atoms such that the nitrogen atoms either are bonded directly to a carbon of an aromatic ring or are themselves members of an aromatic ring. Still more preferably, the aromatic amine is sterically hindered to reduce nucleophilicity. Exemplary mild bases include lutidine (especially 2,6-lutidine), pyrazole, pyridine, unsubstituted imidazole, 2,6-dimethylpyridine, pteridine, pyrazine, pyrimidine, pyridazine, aniline, pyrrole, azepine, methylpyrimidine methylpyrrole, methylpyridazine, and the like. Most preferably, 2,6-lutidine is employed as the mild base in the method.

A variety of acetic anhydride homologs may be employed in the invention as well as acetic anhydride to generate a C-terminal oxazolone moiety. Preferably, such homologs include compounds of the formula:

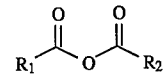

wherein the nature $R_1$ and $R_2$ may vary widely only being constrained to be soluble in the solvents of choice and compatible with the chemistry being employed, e.g. the substituents must be stable to mild bases employed, acid stable (particularly stable to treatment with trifluoroacetic acid), and they must not inhibit the formation of mixed anhydrides in the reaction with carboxyl groups. More preferably, $R_1$ and $R_2$ are selected from the group consisting of alkyl having from 1 to 6 carbon atoms (i.e. $C_1$–$C_6$ alkyl), $C_1$–$C_6$ alkenyl with the proviso that double bonded carbons are not conjugate with the double bonded oxygens, $C_7$–$C_{13}$ alkylaryl with the proviso that double bonded carbons are not conjugate with the double bonded oxygens, and halo-substituted $C_1$–$C_6$ alkyl, $C_1$–$C_6$ alkenyl, or $C_7$–$C_{13}$ alkylaryl with the proviso that double bonded carbons are not conjugate with the double bonded oxygens. Preferably, the halo-substituted substituents have from 1–3 halo-atoms attached selected from the group consisting of fluoro and chloro. Most preferably, $R_1$=$R_2$=methyl.

The solvent used in the activation reaction is preferably an organic or polar aprotic solvent. Suitable solvents include acetonitrile, dimethylformamide (DMF), methylene chloride, ethereal solvents, and the like. Preferably, activation is carried out in tetrahydrofuran (THF).

A variety of thiocyanate reagents can be used for delivering thiocyanate anion to the oxazolone moiety in order to generate a thiohydantoin. Such reagents include ammonium thiocyanate, alkylammonium thiocyanates, metallothiocyanates (e.g., NaSCN, KSCN, AgSCH, and the like) silylisothiocyanates (e.g., trimethylsilylisothiocyanate), and pyridinium thiocyanates. Where the reagent is a metallothiocyanate, the reaction conditions preferably include a crown ether for promoting dissociation of the metal ion from the thiocyanate anion. Preferably, the thiocyanate reagent is an alkylammonium thiocyanate such that the alkyl moiety is sterically hindering to reduce or eliminate the nucleophilicity of the alkylammonium cation. Preferably, the alkyl moiety is a $C_3$–$C_6$ branched alkyl. Most preferably, tetrabutylammonium thiocyanate is employed as the thiocyanate reagent. As discussed more fully below, a thiocyanate reagent having a more nucleophilic conjugate base is desirable in steps for converting the side-chain carboxyls of aspartic and glutamic acid to amides.

Preferably, the method of forming thiohydantoins is employed in C-terminal peptide sequencing. In this application, the C-terminal amino acid residue of an N-protected peptide is the N-protected amino acid to be converted to the thiohydantoin. The sequencing procedure is readily adapted to automated or semiautomated operation, as will be described below.

A C-terminal sequencing method, in accordance with one aspect of the invention, is illustrated in FIGS. 2A–2E. Solid support 22 can be prepared with any surface functional group which can bind the polypeptide, including functional groups placed on the surface by chemical derivatization. For instance, the solid support can be a particle bead having surface amine groups that are suitably derivatized to serve as a site of attachment, e.g., with a bifunctional crosslinking reagent such as disuccinimidyl suberate, although any of a variety of methods for coupling a peptide to a solid support can be employed. Examples of immobilization of peptides on resin and glass beads are presented in U.S. Pat. No. 5,185,266, which disclosure is incorporated herein by reference, and are suitable for practice of the present invention. Preferably, a commerically available derivatized, e.g. carboxy-derivatized, poly(vinylidene difluoride) membrane is used to immobilize sample polypeptides, e.g. ProSpin™ sample preparation cartridge (Applied Biosystems, Foster City, Calif.).

Figure 2A:
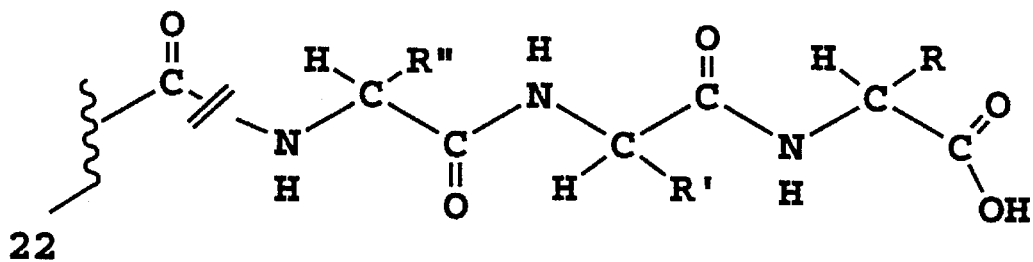
Figure 2B:
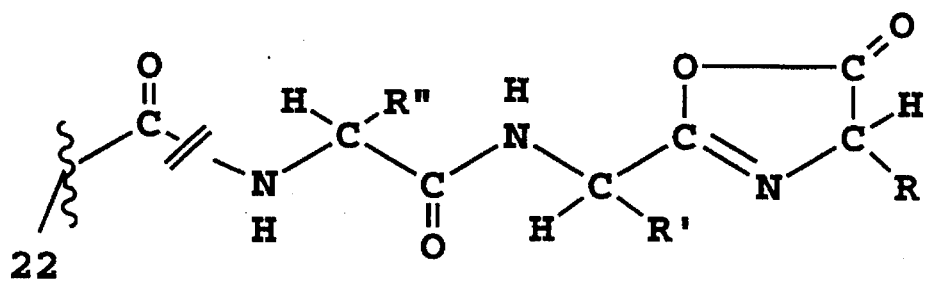
Figure 2C:
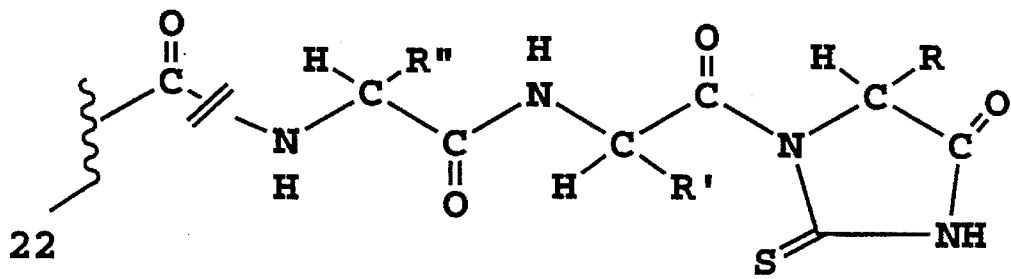

In the first step of the method, the immobilized peptide illustrated in FIG. 2A is reacted with acetic anhydride in the presence of a mild base to form an oxazolone, as discussed in the preceding section. The oxazolone is then reacted with a thiocyanate reagent under acidic conditions, as described above, to produce a thiohydantoin, i.e., a peptidyl thiohydantoin, as illustrated in FIG. 2B. The thiohydantoin is then cleaved from the next-in residue, e.g., by hydrolytic cleavage of the terminal amide bond, under acidic or basic conditions. Preferably, cleavage takes place after the thiohydantoin moiety has been alkylated in accordance with Boyd et al, U.S. Pat. No. 5,185,266. Acidity of the thiocyanate reagent is controlled by delivering an acid, such as trifluoroacetic acid (TFA), as a vapor, e.g. as disclosed in U.S. Pat. No. 5,185,266.

When an alkylating reagent is employed, the cleavage reaction can be performed directly under acidic anhydrous conditions with a thiocyanate anion, as depicted in FIG. 2D. Cleavage in the presence of a thiocyanate reagent is preferred since reaction with the thiocyanate reagent under anhydrous acidic conditions is o effective to form a new TH at the next-in C-terminal amino acid residue, as illustrated in FIG. 2E. This reaction is thought to proceed through the activated peptidyl NCS intermediate shown in FIG. 2D. A metallothiocyanate/crown ether complex under acidic conditions can be used to cleave the alkylated thiohydantoin, with simultaneous formation of the next-in peptidyl thiohydantoin.

Preferably, additional steps are incorporated into the C-terminal sequencing method of the invention to deal with the special problems associated with serine, threonine, aspartate, glutamate, and lysine residues. For example, a carboxyl oxygen in an aspartate residue reacts with the carbonyl carbon in the amide linkage on the C-terminal side of the aspartate residue, thereby severing the polypeptide backbone at that point and forming a cyclic anhydride. In the next cycle of sequencing, the cyclic anhydride can react with thiocyanate reagent to form a new C-terminal thiohydantoin which is co-sequenced along with TH derivatives from the true C-terminus of the polypeptide. The presence of multiple aspartate residues in a polypeptide can be particularly problematic, since internal cleavage of the peptide backbone will lead to the formation of multiple amino acid thiohydantoins in each sequencing step, thereby greatly complicating analysis. Also, the thiohydantoins of aspartate and glutamate residues are typically not detectable, or are detectable only in small amounts, with the side chain carboxylates in unmodified form, e.g. Stark, Biochemisty,7:1796–1807 (1968).

These difficulties with aspartate and glutamate residues can be diminished substantially by amidation of the carboxylate side chains in these residues, particularly prior to beginning the steps of activation/oxazolone formation/thiohydantoin formation/cleavage. Such amidation is preferably carried out by exposing the peptide sample to acetic anhydride in the presence of a mild base, as described above, followed by exposure to an amidating agent, such as piperidine thiocyanate. Preferably, the amidating agent is delivered under neutral or basic conditions to facilitate amidation. Preferably, the side-chain carboxyl groups are convened to piperidine amides.

Serine and threonine residues can also be problematic to C-terminal sequencing, presumably because of interference by the side chain hydroxyl groups of these residues. Accordingly, it is desirable to chemically modify the side chain hydroxyl groups so that such problems are reduced.

Dehydration of serine and threonine residues may be effected by treatment of peptides with phenylisocyanate (PhNCO), e.g. as disclosed by Agarwal and Khorana, J. Am. Chem. Soc., 94:3578 (1972). PhNCO can react with the hydroxyl group of a serine or threonine residue to produce a urethane derivative. Treatment of the urethane derivative with base leads to elimination of $PhNCO_2H$ ($PhNH_2$ and $CO_2$), resulting in formation of the dehydrated analog of serine or threonine. A further advantage of phenylisocyanate treatment is that the ε-amino groups of lysine residues are converted to phenylurea groups. This derivatization reaction thus enhances detection of lysine as a single modified derivative.

Preferably, the side-chain hydroxyls of serinine and threonine and the side-chain amine of lysine are acetylated prior to beginning cycles of sequencing. This is conveniently accomplished with acetic anhydride, as disclosed more fully below.

It is possible using the method of the invention to routinely activate a protein or peptide on an automated sequencer, for example, an Applied Biosystems Sequencer Model 477A in five to thirty minutes at room temperature, although the reaction can also be carried out efficiently at, for example, 55° C., consistent with the reaction temperature of subsequent steps.

The above-detailed sequencing technique is readily automated using equipment ordinarily employed for the automated N-terminal sequencing of peptides. One embodiment of a device for automatically sequencing a peptide from the C-terminal end employs a surface-immobilized peptide contained in a reaction vessel to which fresh solvent and reagents are added, and from which reaction mixtures and solvent washes are removed. The released amino acid thiohydantoin is extracted from the support and transferred to an on-line HPLC for analysis.

The following examples illustrate, but in no way are intended to limit the present invention.

EXAMPLES

Acetic Anhydride Activation of C-terminal Carboxyl Groups.

C-Terminal Sequencing of Test Proteins

Table I lists protein samples and starting amounts that were sequenced from the C-terminus in accordance with the method of the invention:

TABLE I

Figure 7C:
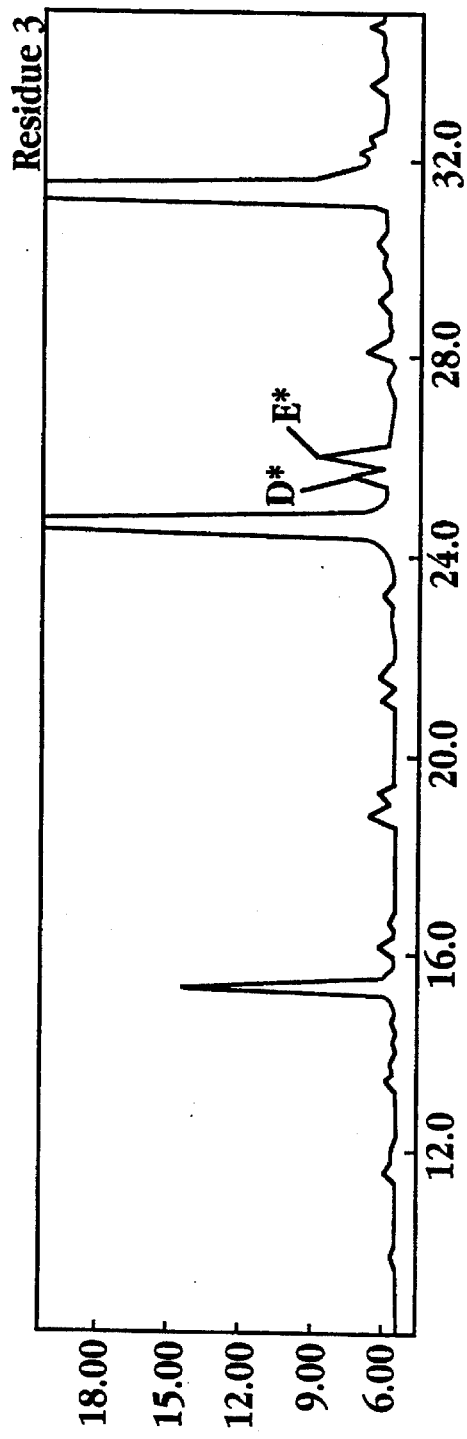
Figure 7D:
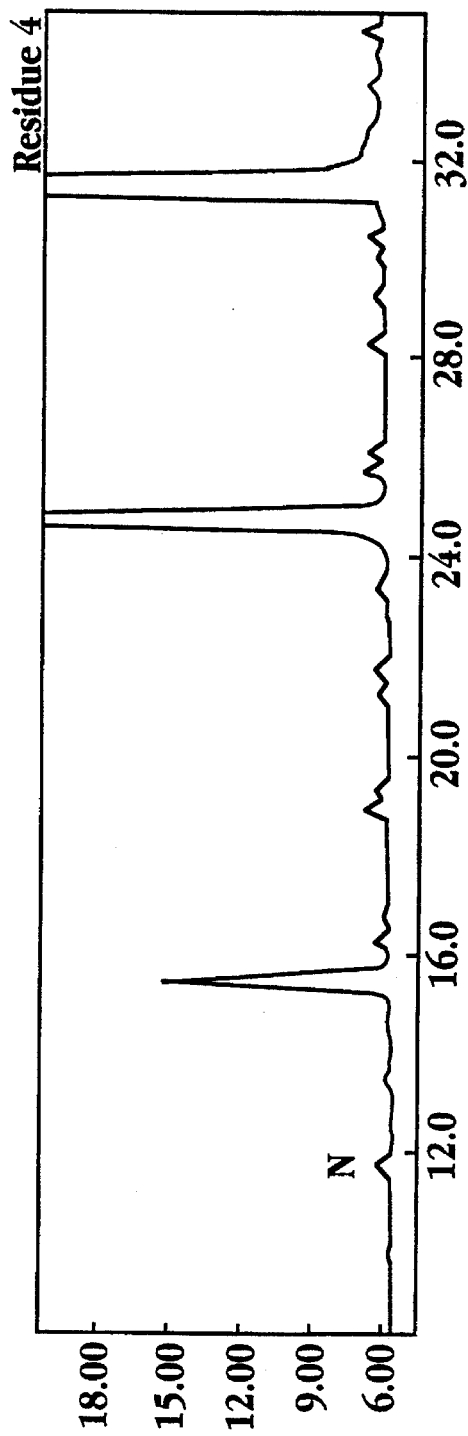

| Protein | Amount | Source | Results |
|---|---|---|---|
| β-lactoglobin | 1 nmole | Sigma | FIG. 3 |
| Cytochrome C | 1 nmole | Sigma | FIG. 4 |
| RNase | 1 nmole | Sigma | FIG. 5 |
| Enolase | 1 nmole | Sigma | FIG. 6 |
| RecA | 1 nmole | recombinant | FIG. 7 |

Samples were non-covalently attached to separate ProSpin (a nonfunctionalized polyvinylidene difluoride membrane) sample cartridges (Applied Biosystems, Foster City, Calif.) using manufacturer's protocols and then sequenced from the C-terminus using an Applied Biosystems Model 477A Protein Sequencer. The sequencing protocol followed was essentially the same as that described in Boyd et al, Anal. Biochemistry, 206:344–352 (1992) and Boyd et al, U.S. Pat. No. 5, 185,266, except for the modifications indicated below. The sequencing protocol consisted of the steps listed in Table III, which is appropriate for proteins having aspartic acid and/or glutamic acid residues (which are amidated with piperidine thiocyanate) and proteins having serine and/or threonine residues (which are acetylated) within their C-terminal regions. Table II lists the reagent reservoir assignments for the model 477A sequencer.

TABLE II

C-terminal reagent configuration for Model 477A Protein Sequencer

| Bottle Position | Reagent | Use |
|---|---|---|
| R1 | tetrabutylammonium thiocyanate | Amidation Cleavage |
| R2 | TFA (vapor) | Activation Cleavage |
| R3 | 2-bromomethyl-naphthalene | Alkylation of TH |
| R4 | acetonitrile | Wash |
| R5 | TFA (liquid) | Standard deprotection |
| X1 | acetic anhydride/ 2,6-lutidine (each 10% in THF) | Carboxyl-activation |
| X2 | Boc-protected alkylated TH standards | Standard |
| S1 | 10% DIEA | Activation Alkylation |
| S2 | piperidine thiocyanate | Amidation TH cleavage |
| S3 | acetonitrile | Transfer solvent |
| S4 | 20% acetonitrile | alkylated TH reconstitution |

The following reaction steps were carried out at 55° C. After the sample was loaded in the sequencer, X1 reagent was delivered to the ProSpin membrane in an amount sufficient to completely wet the membrane. After a 300 sec pause, X1 was delivered again followed by another 300 sec pause. An aliquot of 5% R1 reagent in acetonitrile was delivered to the membrane, followed by exposure to trifluoroacetic acid (TFA) vapor for up to 60 sec, followed by a ten minute pause. This step was repeated, with the membrane being washed with acetonitrile between each reagent delivery. If amidation of the carboxylate groups of aspartate and/or glutamate side chains was desired, an amidation step was included after formation of the peptidyl-TH reagents X1 and S2 (piperidine-HSCN). After a 300 sec pause, X1 and S2 are delivered again. Conditions are left basic, i.e. no TFA delivery. After a 5 min pause, the membrane was washed with acetonitrile. Finally, to acetylate hydroxyl side-chains of serine and threonine, 10% DIEA is delivered, followed by reagent X1 and up a 900 sec pause. (Acetylation can be reiterated during sequencing if required).

At each sequencing cycle, the C-terminal thiohydantoin was reacted with an alkylating agent as taught in U.S. Pat. No. 5,185,266. Tetrabutylammonium thiocyanate and TFA vapor are the used to cleave the thiohydantoin adduct from the remaining protein. The cleaved thiohydantoin adducts were isolated and detected as taught in U.S. Pat. No. 5, 185,266.

Figure 3A:
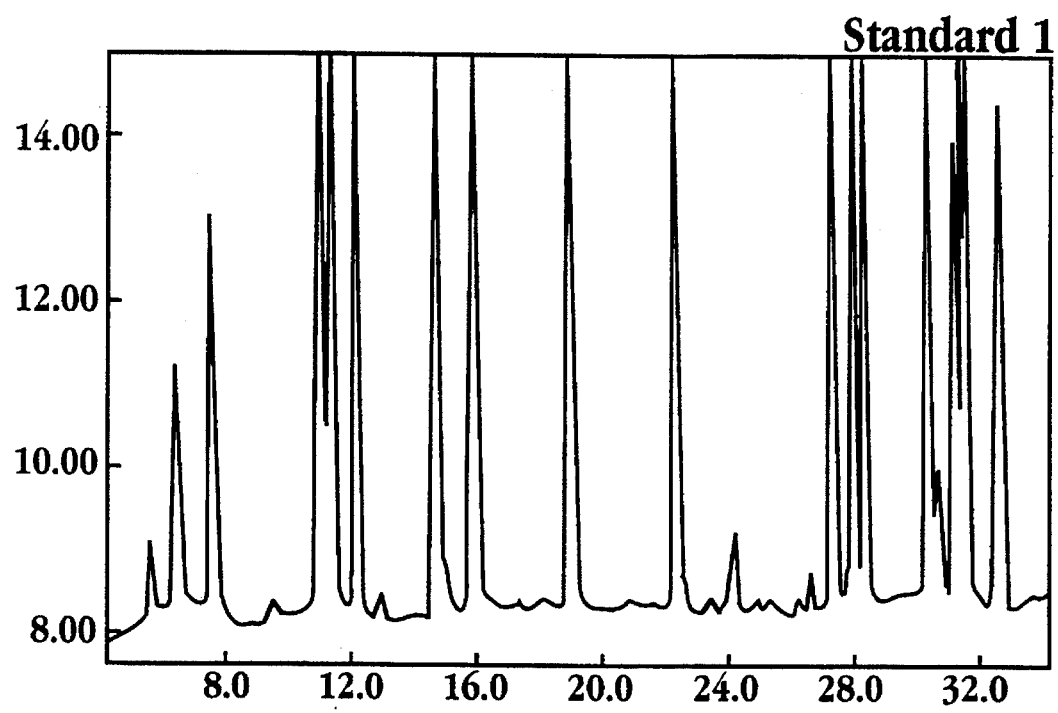
FIGS. 3A–3H are chromatograms of cleaved arylalkylated amino acid thiohydantoins from the C-terminal sequencing of β-lactoglobulin.
Figure 3B:
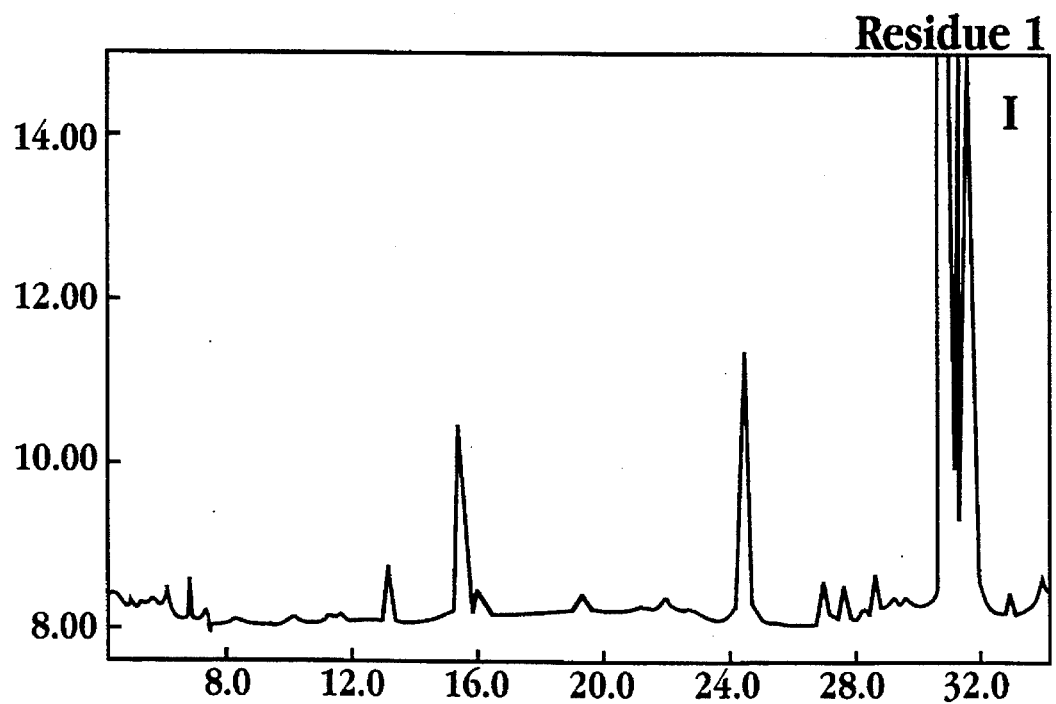
Figure 3C:
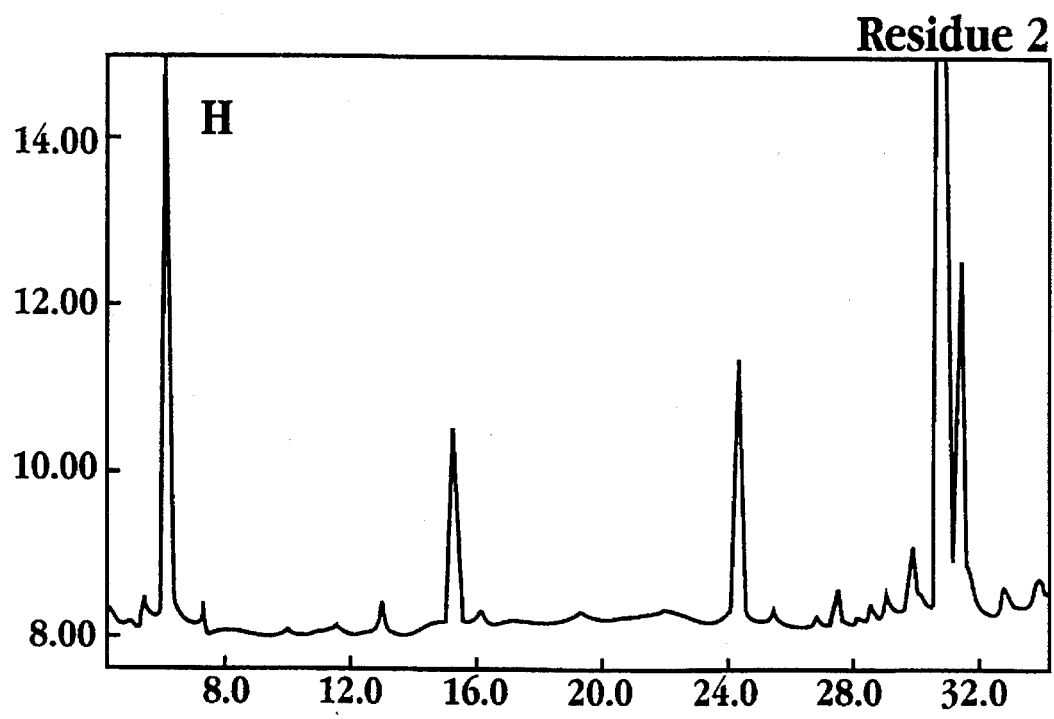
Figure 3D:
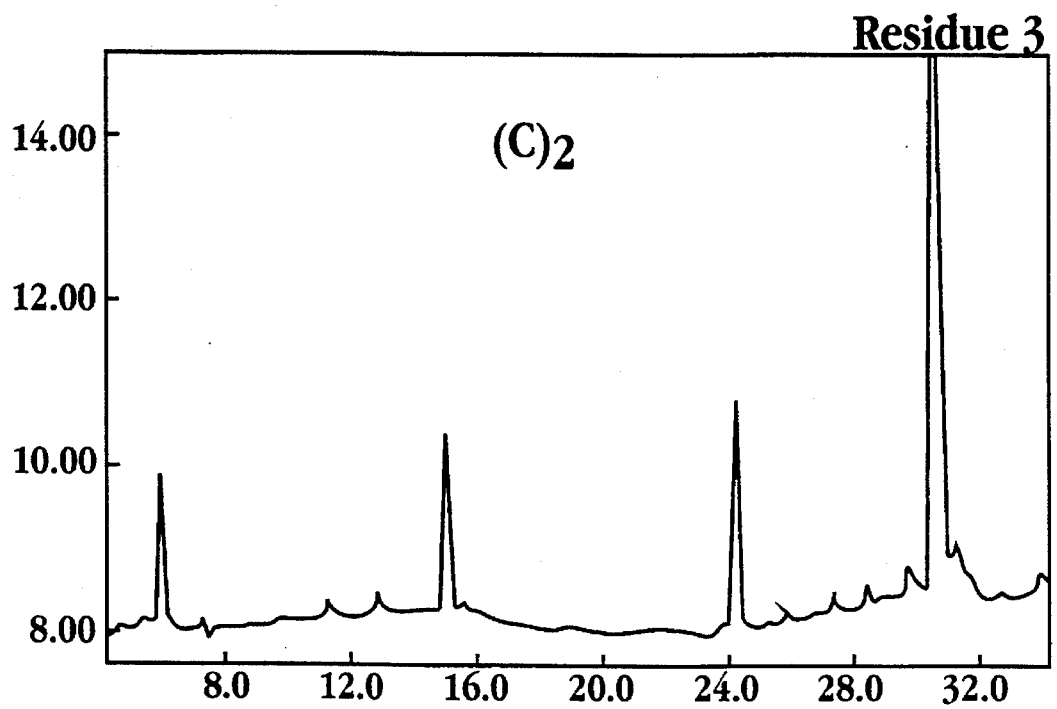
Figure 3E:
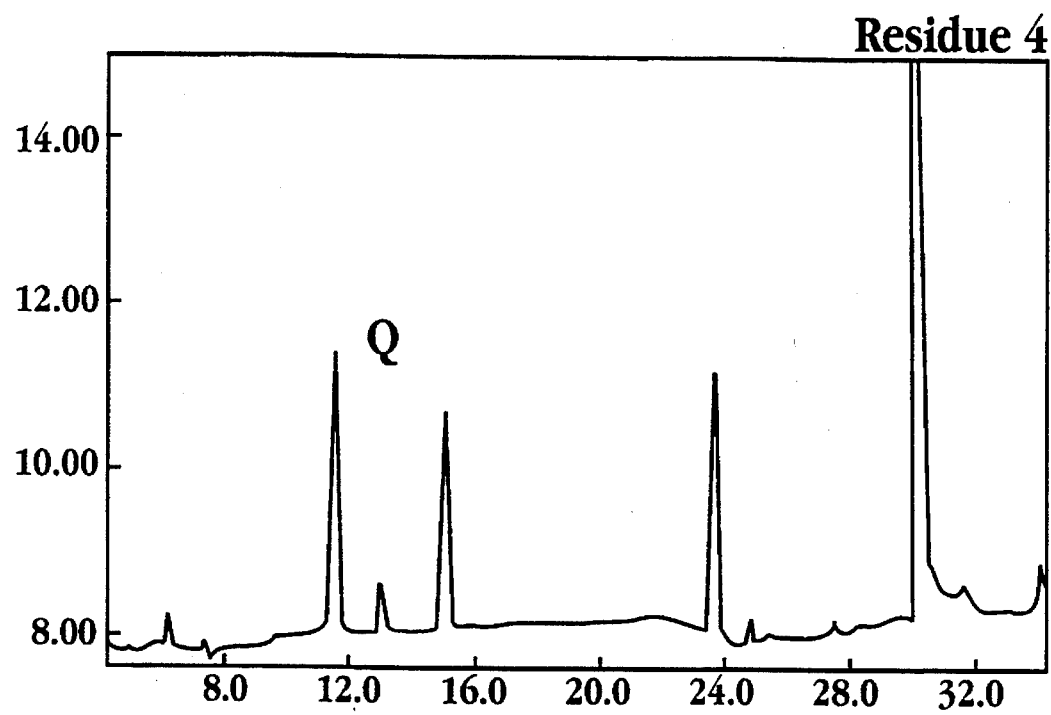
Figure 3F:
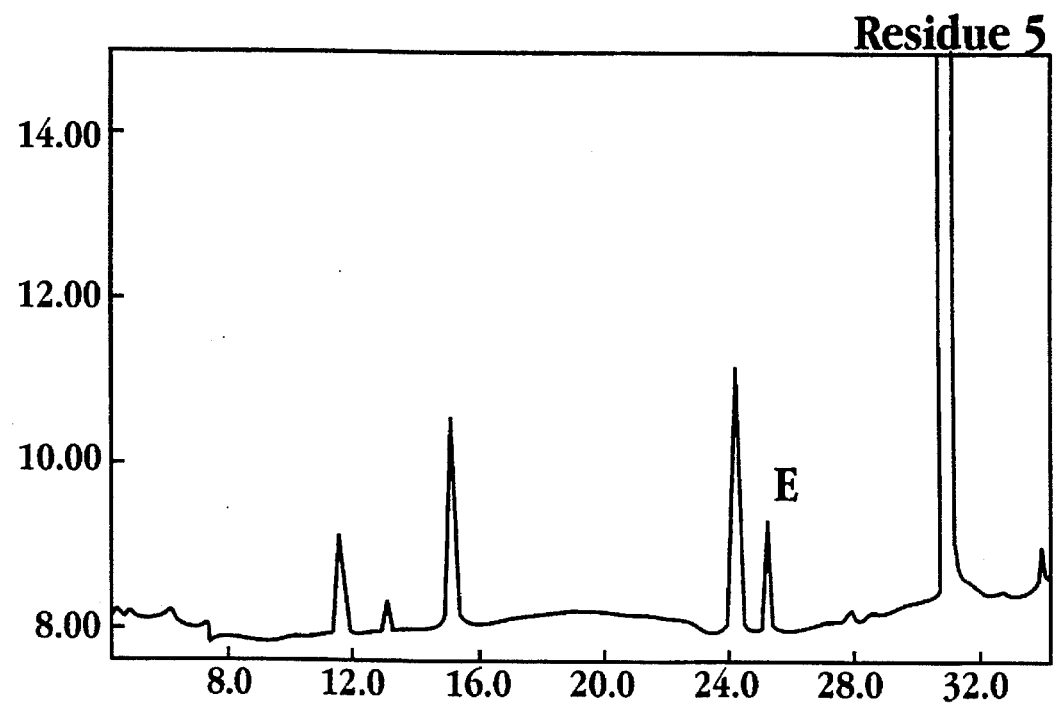
Figure 3G:
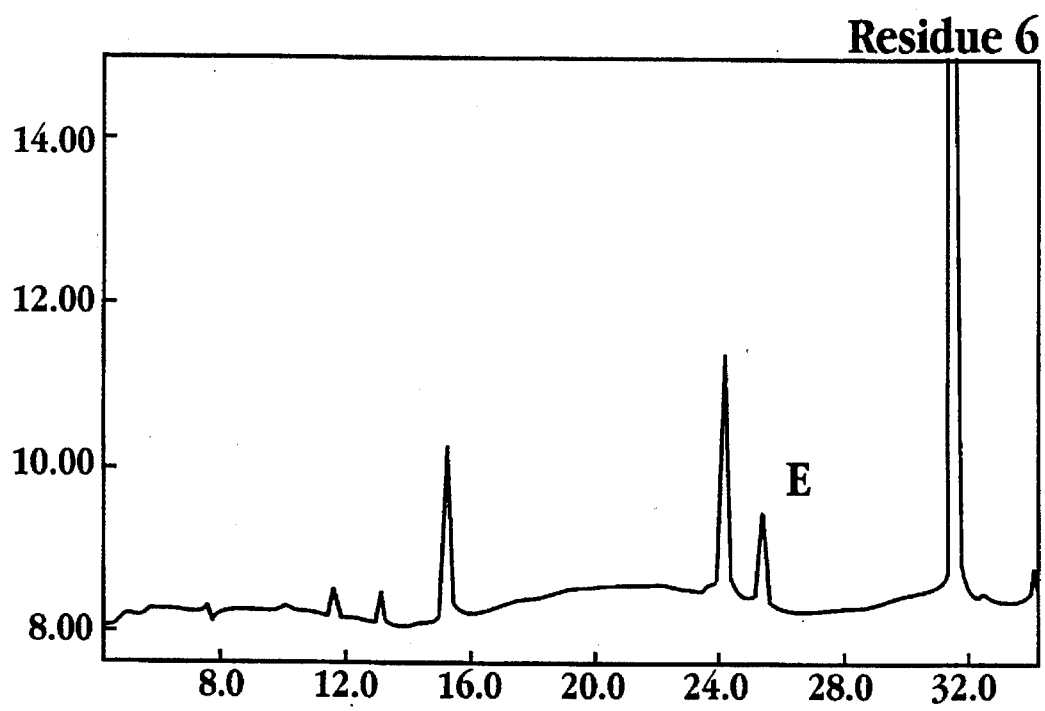
Figure 3H:
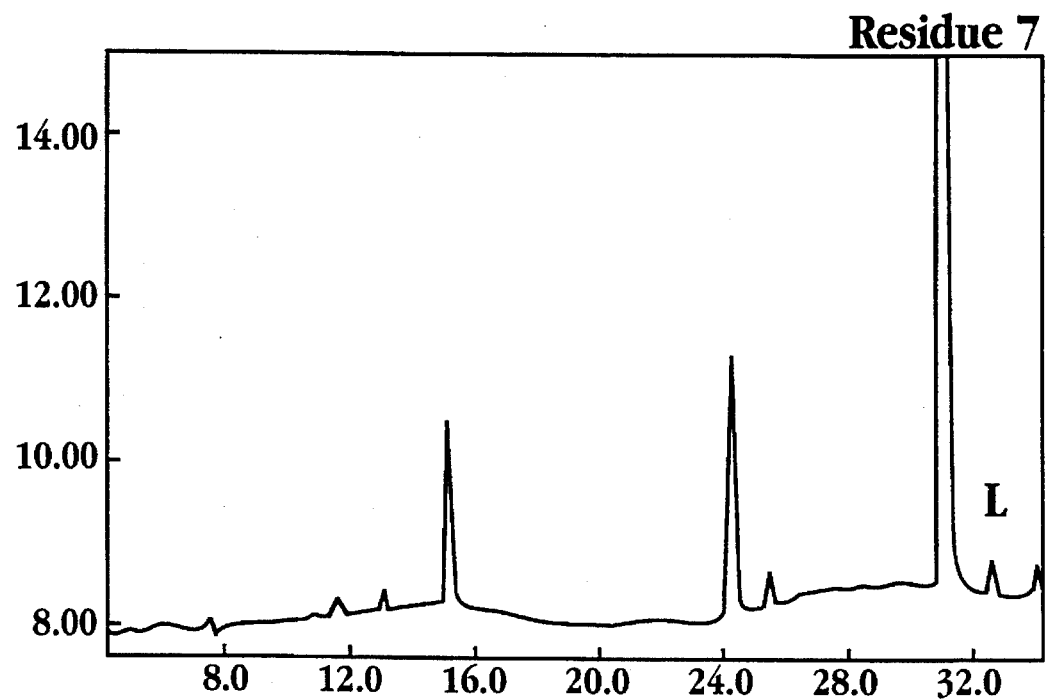
Figure 4A:
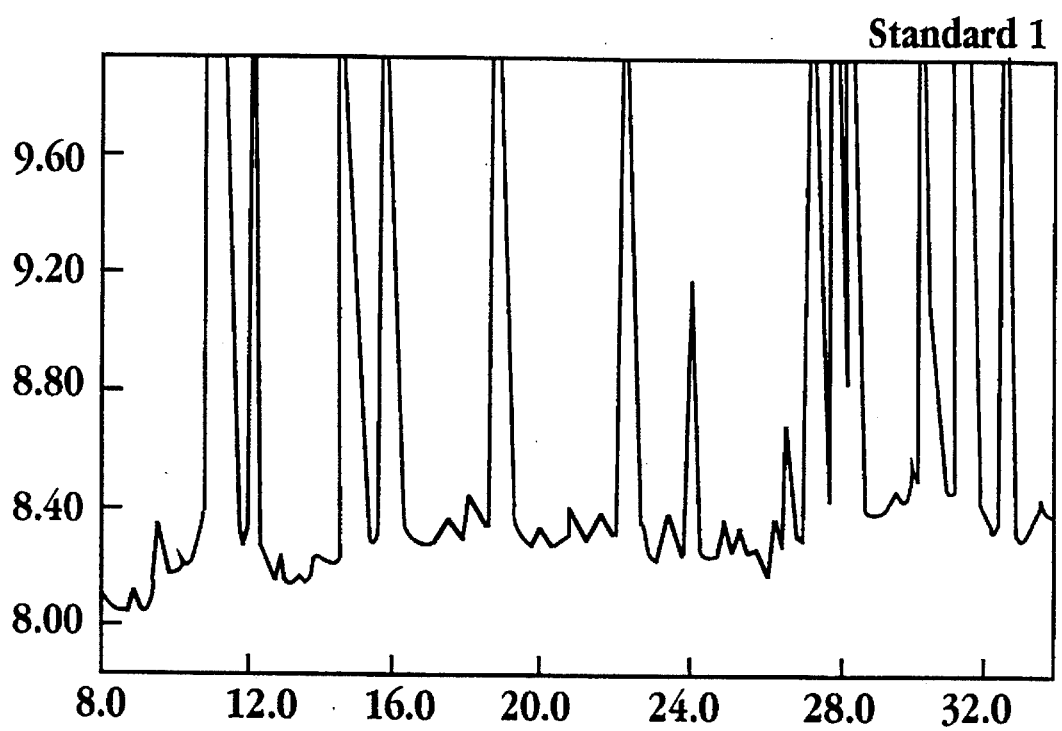
FIGS. 4A–4H are chromatograms of cleaved arylalkylated amino acid thiohydantoins from the C-terminal sequencing of cytochrome C.
Figure 4B:
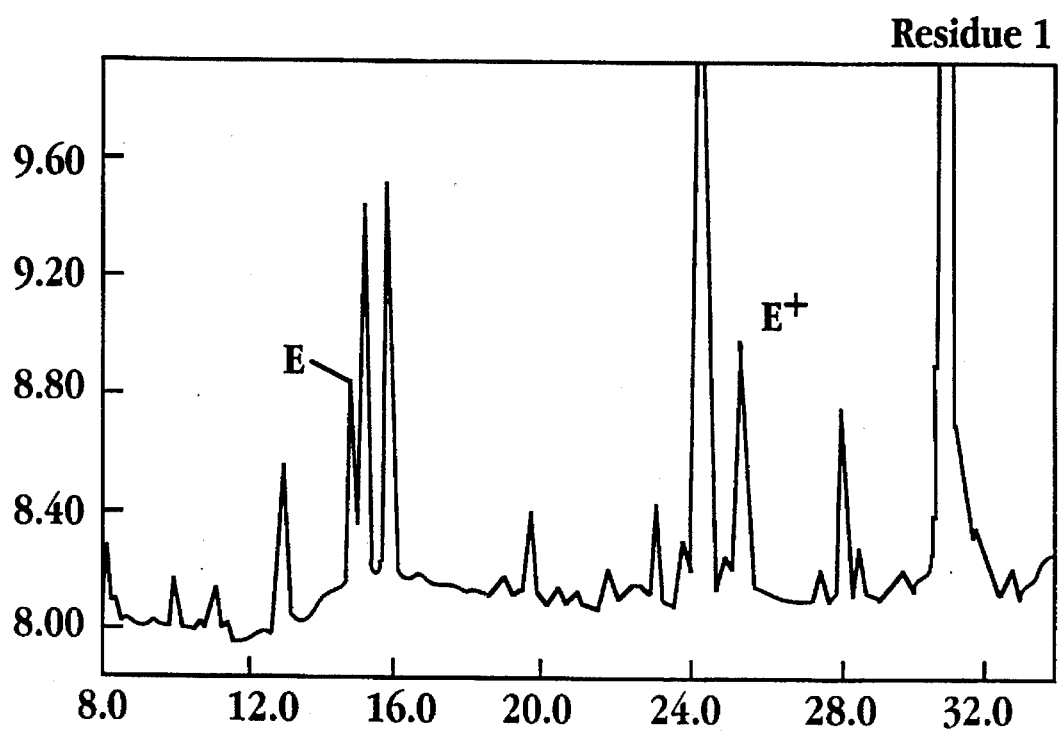
Figure 4C:
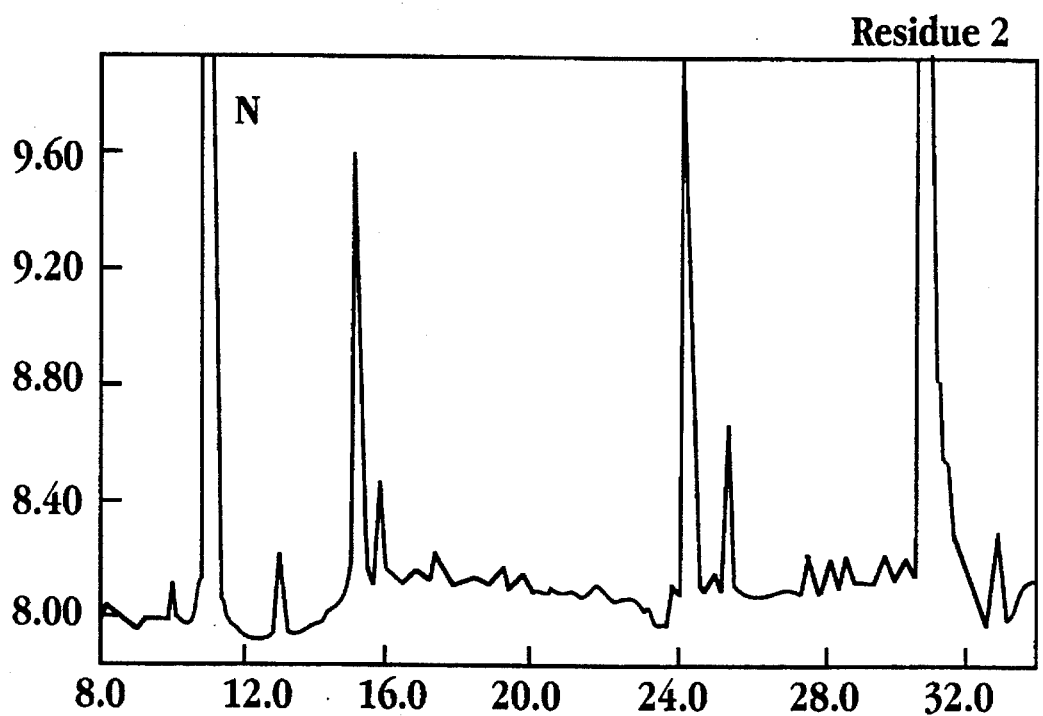
Figure 4D:
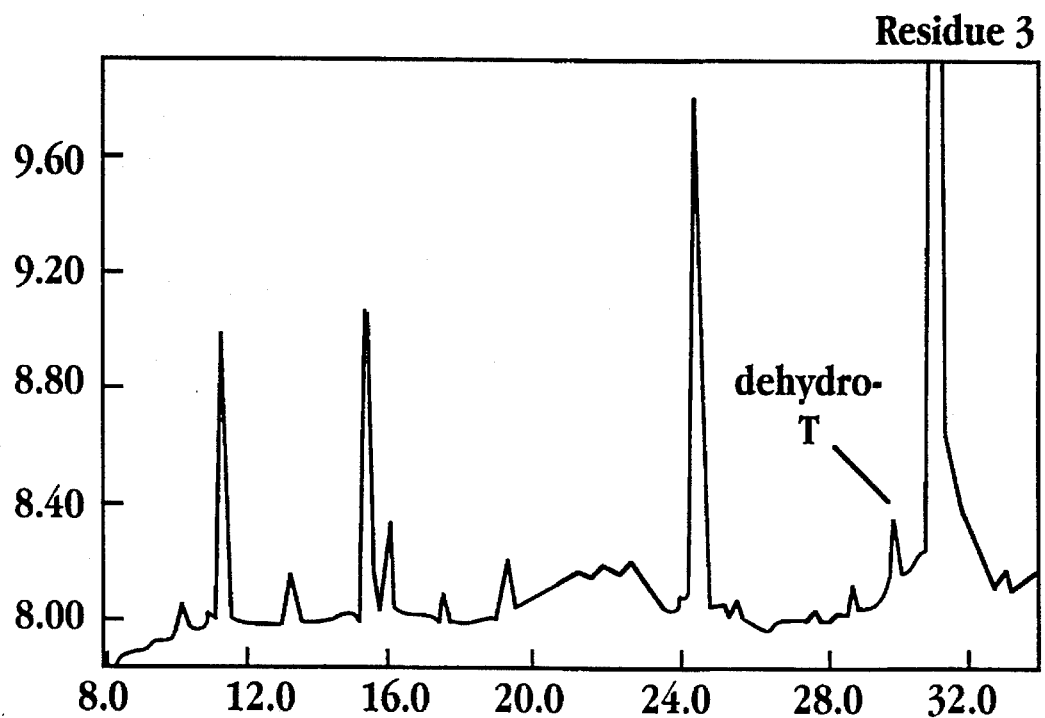
Figure 4E:
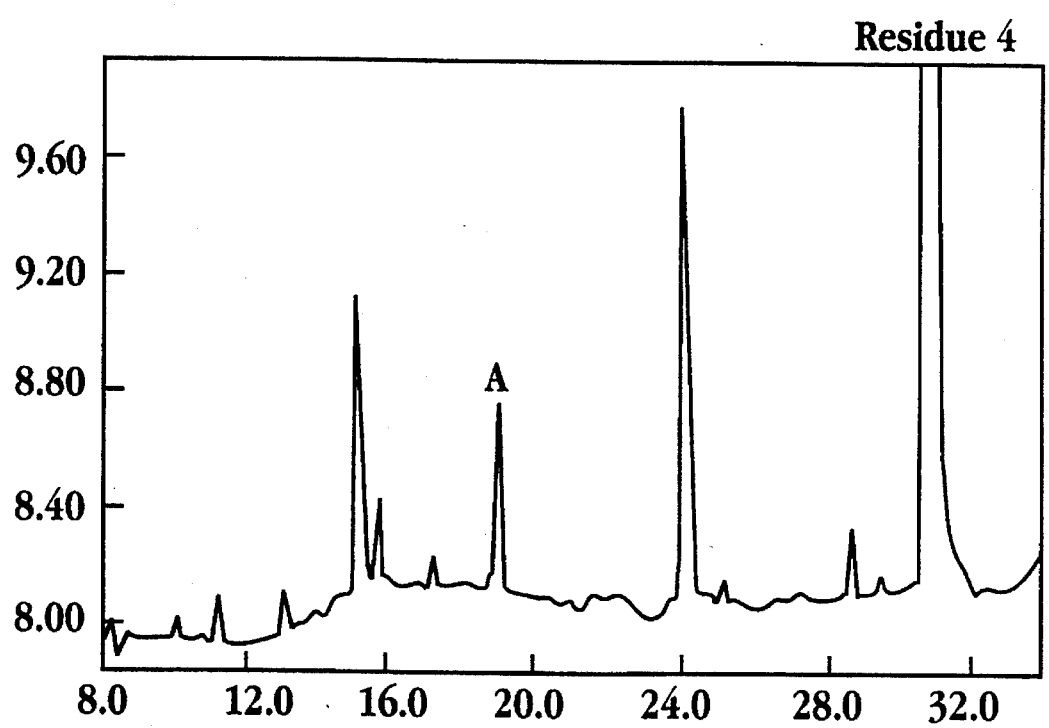
Figure 4F:
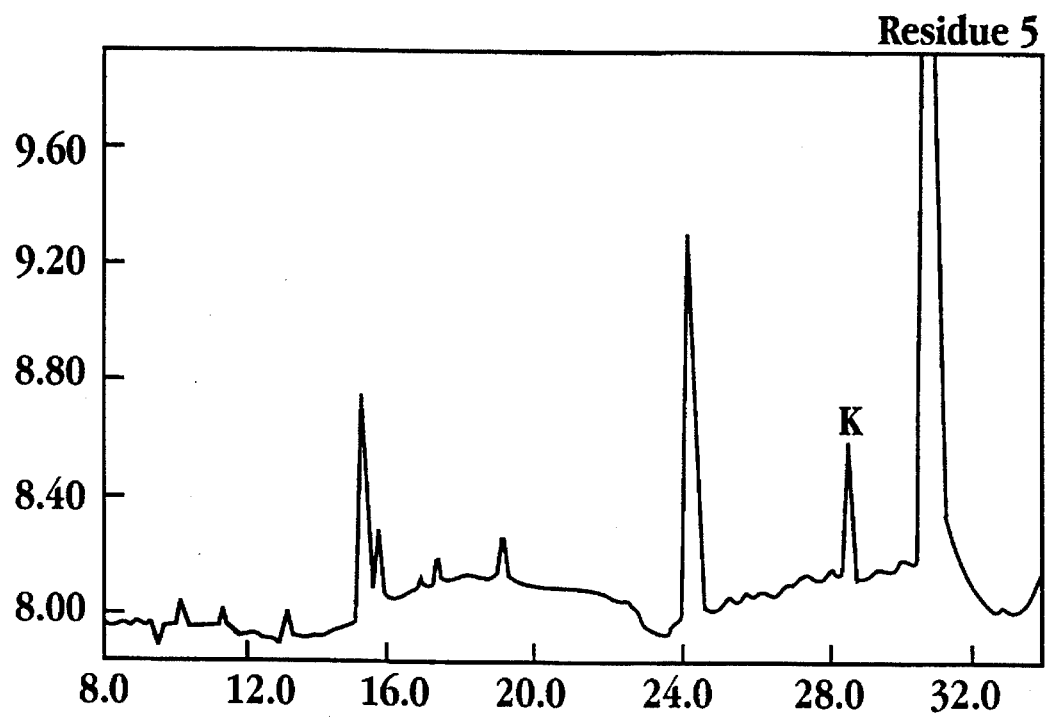
Figure 4G:
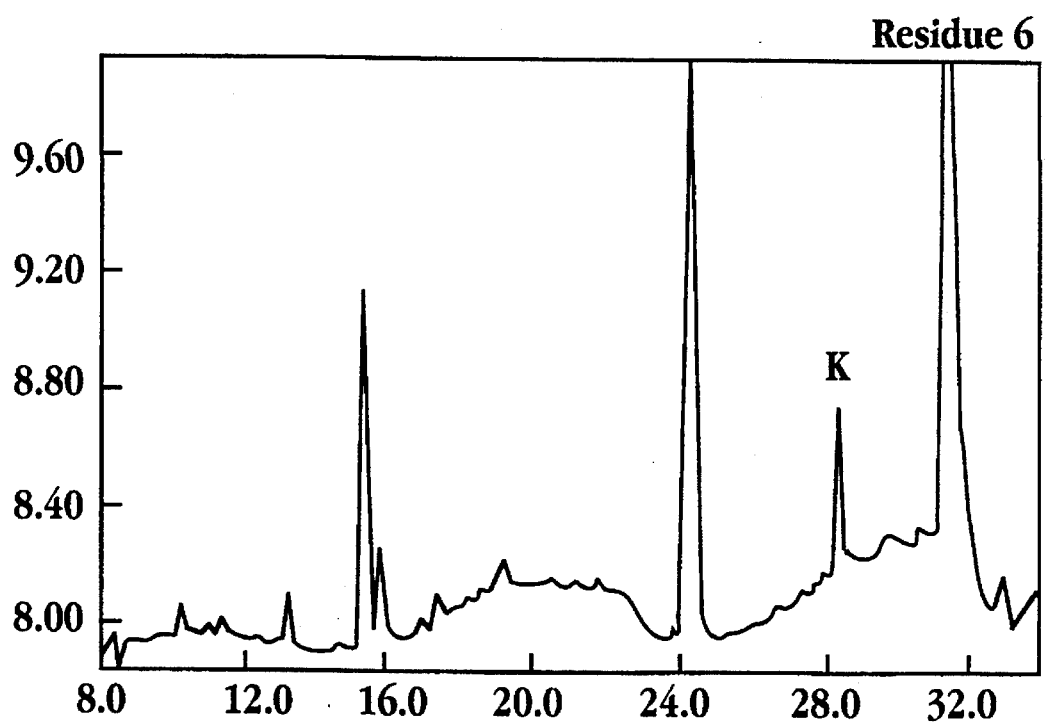
Figure 4H:
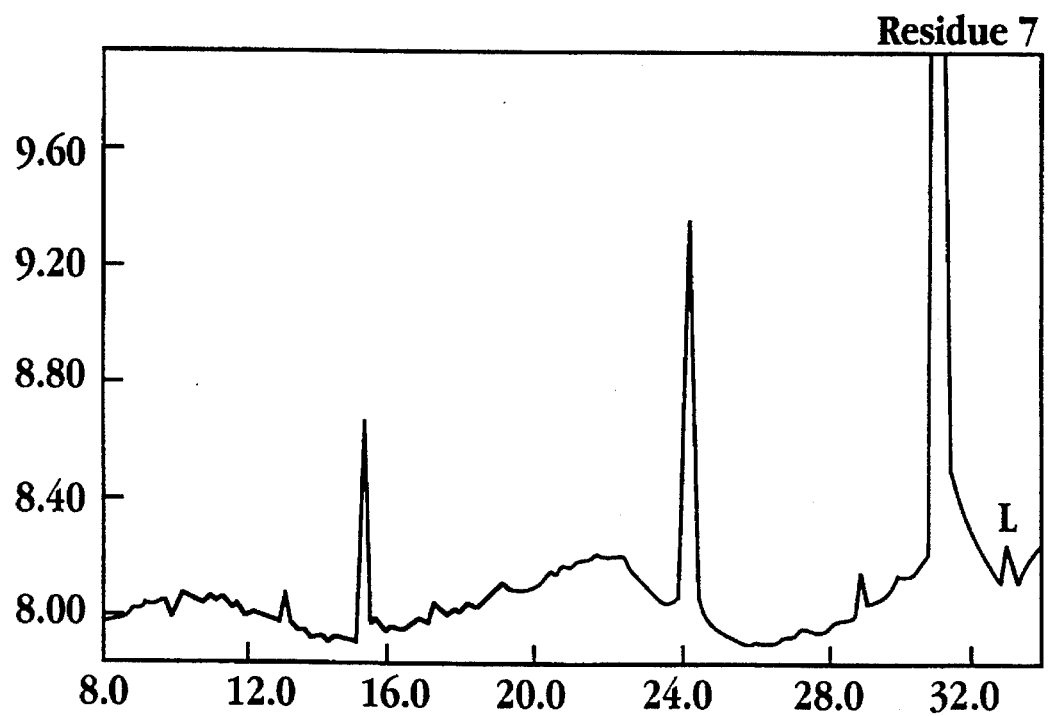
Figure 5A:
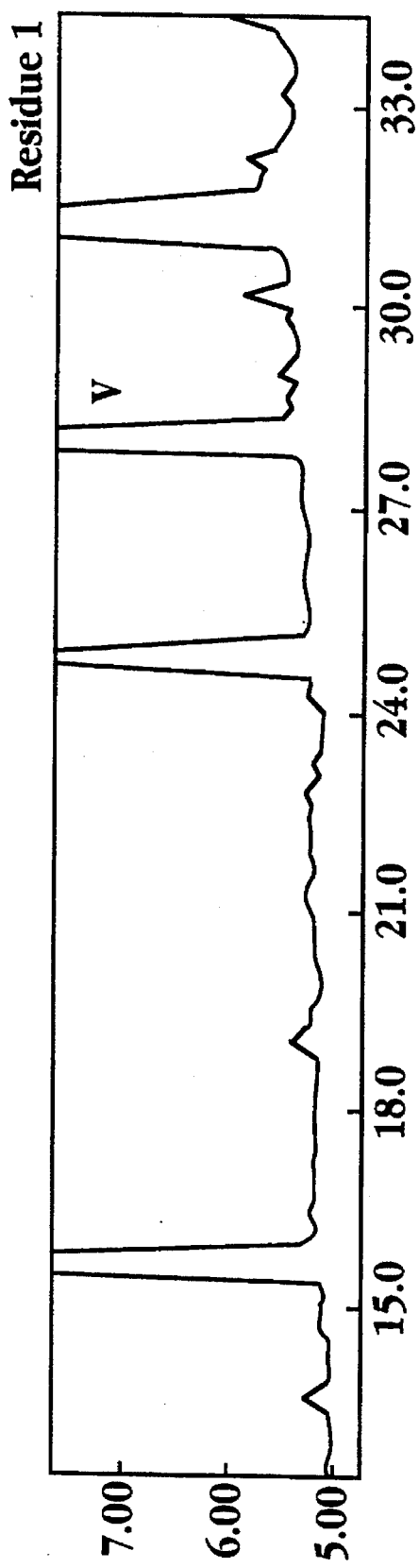
FIGS. 5A–5E are chromatograms of cleaved arylalkylated amino acid thiohydantoins from the C-terminal sequencing of RNase.
Figure 5B:
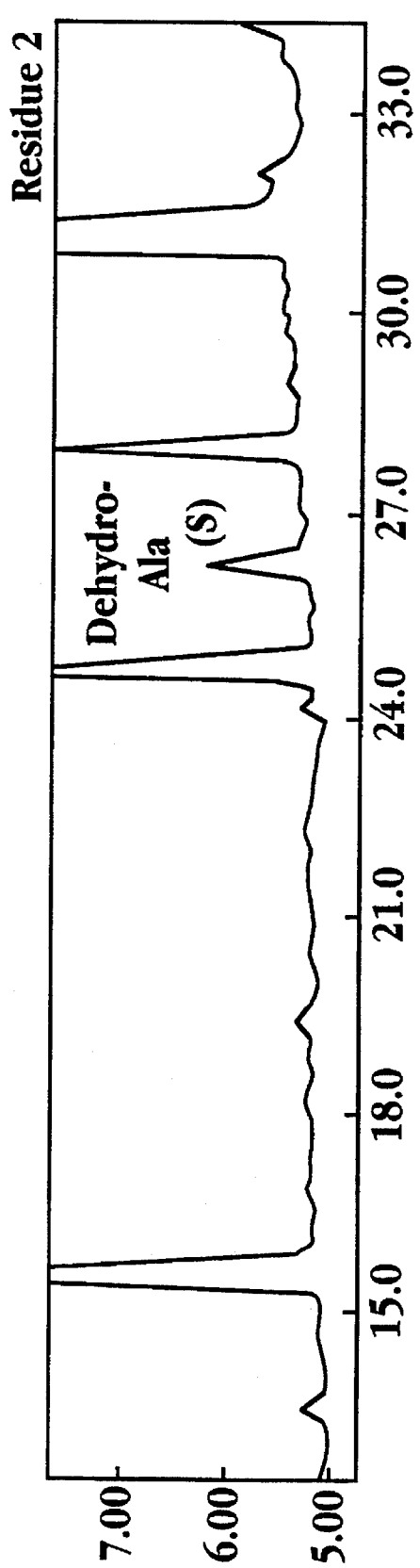
Figure 5C:
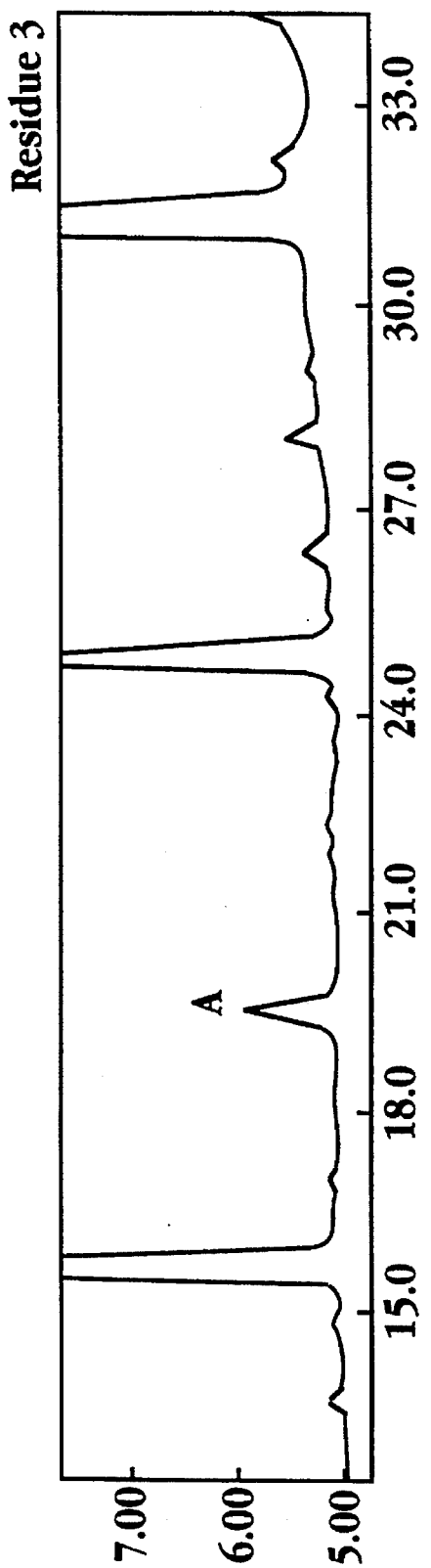
Figure 5D:
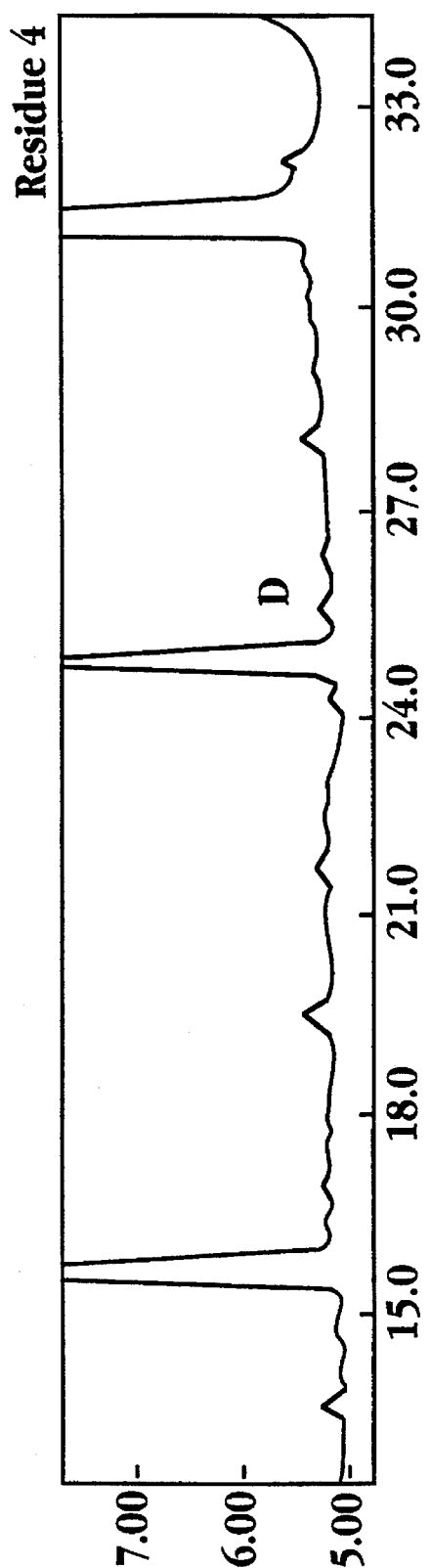
Figure 5E:
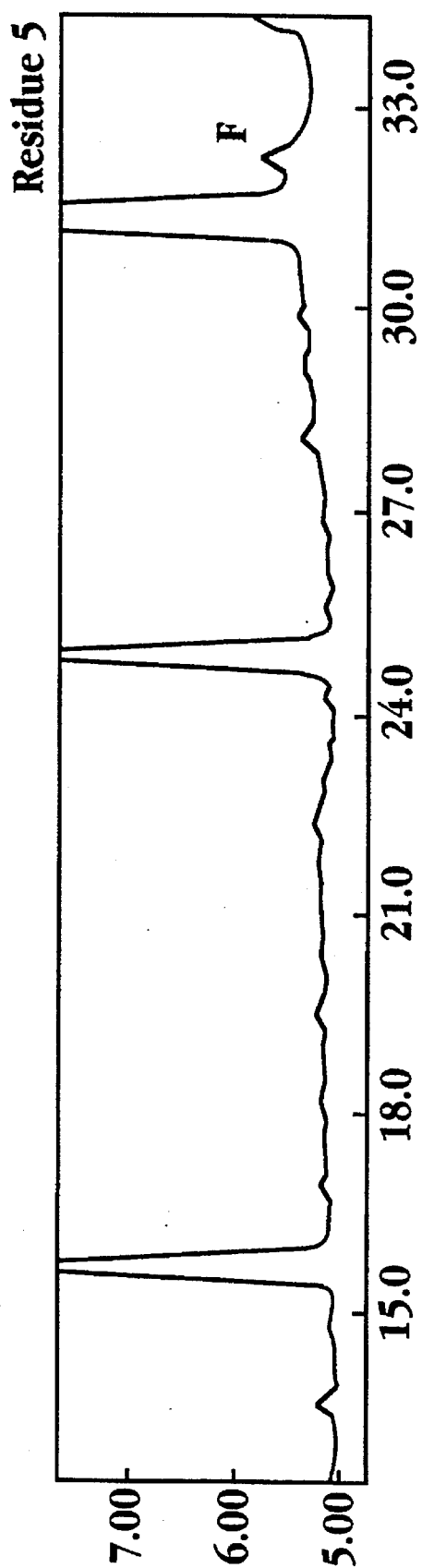

FIGS. 3A and 4A are chromatograms of the alkylthiohydantoin amino acid standards. In FIGS. 3B through 7D, peaks corresponding to the cleaved alkylthiohydantoin amino acids are indicated by the single letter symbol of their associated amino acid. "$(C)_2$" indicates a cysteine residue. "E*" and "D*" indicate a piperidine amide of glutamic acid and aspartic acid, respectively. "dehydro-T" indicates a dehydrated threonine. In FIG. 6B the labeled peak is believed to be an acetylated lysine thiohydantoin.

TABLE III

Model 477A Cycle Steps for Lys-, Ser-, Thr-, Asp- and/or Glu- Containing Protein or Peptide Samples

| Step | Function | Fxn # | Ualue | Elapsed Time |
|---|---|---|---|---|
| 1 | Deliver S3 | 20 | 200 | 3 min 20 sec |
| 2 | Argon Dry | 29 | 200 | 6 min 40 sec |
| 3 | Prep X1 | 10 | 6 | 6 min 46 sec |
| 4 | Deliver X1 | 11 | 3 | 6 min 49 sec |
| 5 | Argon Dry | 29 | 8 | 6 min 57 sec |
| 6 | Pause | 33 | 300 | 11 min 57 sec |
| 7 | Deliver S3 | 20 | 60 | 12 min 57 sec |
| 8 | Argon Dry | 29 | 20 | 13 min 17 sec |
| 9 | Prep X1 | 10 | 6 | 13 min 23 sec |
| 10 | Deliver X1 | 11 | 3 | 13 min 26 sec |
| 11 | Argon Dry | 29 | 8 | 13 min 34 sec |
| 12 | Pause | 33 | 300 | 18 min 34 sec |
| 13 | Deliver S3 | 20 | 60 | 19 min 34 sec |
| 14 | Argon Dry | 29 | 20 | 19 min 34 sec |
| 15 | Prep R1 | 1 | 6 | 20 min 0 sec |
| 16 | Deliver R1 | 2 | 3 | 20 min 3 sec |
| 17 | Argon Dry | 29 | 8 | 20 min 11 sec |
| 18 | Load S3 | 21 | 20 | 20 min 31 sec |

TABLE III-continued

Model 477A Cycle Steps for Lys-, Ser-, Thr-, Asp- and/or Glu- Containing Protein or Peptide Samples

| Step | Function | Fxn # | Ualue | Elapsed Time |
|------|----------|-------|-------|--------------|
| 19 | Block Flush | 30 | 20 | 20 min 51 sec |
| 20 | Prep R2 | 4 | 6 | 20 min 57 sec |
| 21 | Deliver R2 | 5 | 40 | 21 min 37 sec |
| 22 | Load S3 | 21 | 20 | 21 min 57 sec |
| 23 | Block Flush | 30 | 20 | 22 min 17 sec |
| 24 | Pause | 33 | 600 | 32 min 17 sec |
| 25 | Deliver S3 | 20 | 30 | 32 min 47 sec |
| 26 | Pause | 33 | 20 | 33 min 7 sec |
| 27 | Deliver S3 | 20 | 30 | 33 min 37 sec |
| 28 | Pause | 33 | 20 | 33 min 57 sec |
| 29 | Argon Dry | 29 | 60 | 34 min 57 sec |
| 30 | Deliver S3 | 20 | 30 | 35 min 57 sec |
| 31 | Pause | 33 | 20 | 35 min 47 sec |
| 32 | Argon Dry | 29 | 60 | 36 min 47 sec |
| 33 | Prep R1 | 1 | 6 | 36 min 53 sec |
| 34 | Deliver R1 | 2 | 3 | 36 min 56 sec |
| 35 | Argon Dry | 29 | 8 | 37 min 4 sec |
| 36 | Load S3 | 21 | 20 | 37 min 24 sec |
| 37 | Block Flush | 30 | 20 | 37 min 44 sec |
| 38 | Prep R2 | 4 | 6 | 37 min 50 sec |
| 39 | Deliver R2 | 5 | 40 | 38 min 30 sec |
| 40 | Load S3 | 21 | 20 | 38 min 50 sec |
| 41 | Block Flush | 30 | 20 | 39 min 10 sec |
| 42 | Pause | 33 | 600 | 49 min 10 sec |
| 43 | Deliver S3 | 20 | 30 | 49 min 40 sec |
| 44 | Pause | 33 | 20 | 50 min 0 sec |
| 45 | Argon Dry | 29 | 60 | 51 min 0 sec |
| 46 | Deliver S3 | 20 | 30 | 51 min 30 sec |
| 47 | Pause | 33 | 20 | 51 min 50 sec |
| 48 | Argon Dry | 29 | 20 | 52 min 10 sec |
| 49 | Deliver S3 | 20 | 30 | 52 min 40 sec |
| 50 | Pause | 33 | 20 | 53 min 0 sec |
| 51 | Argon Dry | 29 | 20 | 53 min 20 sec |
| 52 | Prep X1 | 10 | 6 | 53 min 26 sec |
| 53 | Deliver X1 | 11 | 3 | 53 min 29 sec |
| 54 | Argon Dry | 29 | 8 | 53 min 37 sec |
| 55 | Pause | 33 | 300 | 58 min 37 sec |
| 56 | Prep S2 | 16 | 20 | 58 min 57 sec |
| 57 | Load S2 | 18 | 6 | 59 min 3 sec |
| 58 | Argon Dry | 29 | 9 | 59 min 12 sec |
| 59 | Pause | 33 | 300 | 64 min 12 sec |
| 60 | Prep S3 | 19 | 20 | 64 min 32 sec |
| 61 | Deliver S3 | 20 | 20 | 64 min 52 sec |
| 62 | Argon Dry | 29 | 20 | 65 min 12 sec |
| 63 | Deliver S3 | 20 | 20 | 65 min 32 sec |
| 64 | Pause | 33 | 20 | 65 min 52 sec |
| 65 | Argon Dry | 29 | 20 | 66 min 12 sec |
| 66 | Prep X1 | 10 | 6 | 66 min 18 sec |
| 67 | Deliver X1 | 11 | 3 | 66 min 21 sec |
| 68 | Argon Dry | 29 | 8 | 66 min 29 sec |
| 69 | Pause | 33 | 300 | 71 min 29 sec |
| 70 | Prep S2 | 16 | 20 | 71 min 49 sec |
| 71 | Load S2 | 18 | 6 | 71 min 55 sec |
| 72 | Argon Dry | 29 | 8 | 72 min 3 sec |
| 73 | Pause | 33 | 300 | 77 min 3 sec |
| 74 | Deliver S3 | 20 | 20 | 77 min 23 sec |
| 75 | Pause | 33 | 20 | 77 min 43 sec |
| 76 | Argon Dry | 29 | 20 | 78 min 3 sec |
| 77 | Deliver S3 | 20 | 20 | 78 min 23 sec |
| 78 | Pause | 33 | 20 | 78 min 43 sec |
| 79 | Argon Dry | 29 | 20 | 79 min 3 sec |
| 80 | Prep S1 | 13 | 20 | 79 min 23 sec |
| 81 | Deliver S1 | 14 | 10 | 79 min 33 sec |
| 82 | Pause | 33 | 20 | 79 min 53 sec |
| 83 | Argon Dry | 29 | 8 | 80 min 1 sec |
| 84 | Prep X1 | 10 | 6 | 80 min 7 sec |
| 85 | Deliver X1 | 11 | 3 | 80 min 10 sec |
| 86 | Argon Dry | 29 | 8 | 80 min 18 sec |
| 87 | Pause | 33 | 900 | 95 min 18 sec |
| 88 | Prep S3 | 19 | 20 | 95 min 38 sec |
| 89 | Deliver S3 | 20 | 20 | 95 min 58 sec |
| 90 | Pause | 33 | 20 | 96 min 18 sec |
| 91 | Argon Dry | 29 | 20 | 96 min 38 sec |
| 92 | Deliver S3 | 20 | 20 | 96 min 58 sec |
| 93 | Pause | 33 | 20 | 97 min 18 sec |
| 94 | Argon Dry | 29 | 20 | 97 min 38 sec |
| 95 | Deliver S3 | 20 | 20 | 97 min 58 sec |
| 96 | Pause | 33 | 20 | 98 min 18 sec |
| 97 | Argon Dry | 29 | 60 | 99 min 18 sec |

While the invention has been described with reference to specific methods and embodiments, it will be appreciated that various modifications and changes may be made without departing from the invention.

It is claimed:

1. A method of forming a thiohydantoin moiety at tile C-terminus of a polypeptide, the method comprising the steps of:

treating the polypeptide with an anhydride under basic conditions such that an oxazolone moiety is formed at the C-terminus of the polypeptide, the anhydride being defined by tile formula:

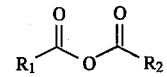

wherein $R_1$ and $R_2$ are selected from the group consisting of $C_1-C_6$ alkyl, $C_1-C_6$ alkenyl with the proviso that double bonded carbons are not conjugate with the double bonded oxygens, $C_7-C_{13}$ alkylaryl with the proviso that double bonded carbons are not conjugate with the double bonded oxygens, and halo-substituted $C_1-C_6$ alkyl, $C_1-C_6$ alkenyl, or $C_7-C_{13}$ alkylaryl with the proviso that double bonded carbons are not conjugate with the double bonded oxygens; and treating the polypeptide with thiocyanate under acidic conditions so that the oxazolone moiety is converted into a thiohydantoin moiety.

2. The method of claim 1 wherein said basic conditions are maintained with an organic base having a $K_b$ in the range of between about $10^{-7}$ to about $10^{-12}$ 3. The method of claim 2 wherein said organic base is an aromatic amine containing from 1 to 4 nitrogen atoms such that every nitrogen atom is either bonded directly to a carbon of an aromatic ring or is a member of an aromatic ring.

4. The method of claim 3 wherein said organic base is selected from the group consisting of lutidine, pyrazole, pyridine, imidazole, 2,6-dimethylpyridine, pteridine, pyrazine, pyrimidine, pyridazine, aniline, pyrrole, azepine, methylpyrimidine methylpyrrole, and methylpyridazine.

5. The method of claim 4 wherein said organic base is 2,6-lutidine and said anhydride is acetic anhydride.

6. The method of claim 5 wherein said step of treating with thiocyanate includes treating said polypeptide with tetrabutylammonium thiocyanate.

7. A method of determining the sequence amino acids in the C-terminal region of a polypeptide, the method comprising the steps of:

(a) treating the polypeptide with an anhydride under basic conditions so that an oxazolone moiety is formed at the C-terminus of the polypeptide, the anhydride having the formula:

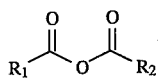

wherein $R_1$ and $R_2$ are selected from the group consisting of $C_1$–$C_6$ alkyl, $C_1$–$C_6$ alkenyl with the proviso that double bonded carbons are not conjugate with the double bonded oxygens, $C_7$–$C_{13}$ alkylaryl with the proviso that double bonded carbons are not conjugate with the double bonded oxygens, and halo-substituted $C_1$–$C_6$ alkyl, $C_1$–$C_6$ alkenyl, or $C_7$–$C_{13}$ alkylaryl with the proviso that double bonded carbons are not conjugate with the double bonded oxygens;

(b) treating the oxazolone moiety at the C-terminus of the polypeptide with thiocyanate under acidic conditions to form an amino acid thiohydantoin;

(c) cleaving the amino acid thiohydantoin from the polypeptide;

(d) identifying the cleaved amino acid thiohydantoin; and (e) repeating steps (a) through (d) until the amino acids of the C-terminal region of the polypeptide are determined.

8. The method of claim 7 wherein said polypeptide includes a side-chain carboxyl group, the method further comprising the steps of:

treating said polypeptide with acetic anhydride under basic conditions to form a mixed anhydride between the side-chain carboxyl group and the acetic anhydride; and treating the mixed anhydride with piperidine thiocyanate under non-acidic conditions to form a piperidine amide.

9. The method of claim 7 wherein said polypeptide includes a side-chain hydroxyl group, the method further comprising the step of acetylating the side-chain hydroxyl group.

10. The method of claim 7 wherein said step of cleaving includes alkylating said amino acid thiohydantoin.

11. The method of claim 7 wherein said anhydride is acetic anhydride and said basic conditions are maintained with an organic base having a $K_b$ in the range of between about $10^{-7}$ to about $10^{-12}$.

12. The method of claim 11 wherein said organic base is lutidine.

13. A method of identifying the C-terminal amino acid of a polypeptide, the method comprising the steps of:

(a) treating the polypeptide with an anhydride under basic conditions so that an oxazolone moiety is formed at the C-terminus of the polypeptide, the anhydride being defined by the formula:

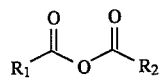

wherein $R_1$ and $R_2$ are selected from the group consisting of $C_1$–$C_6$ alkyl, $C_1$–$C_6$ alkenyl with the proviso that double bonded carbons are not conjugate with the double bonded oxygens, $C_7$–$C_{13}$ alkylaryl with the proviso that double bonded carbons are not conjugate with the double bonded oxygens, and halo-substituted $C_1$–$C_6$ alkyl, $C_1$–$C_6$ alkenyl, or $C_7$–$C_{13}$ alkylaryl with the proviso that double bonded carbons are not conjugate with the double bonded oxygens;

(b) treating the oxazolone moiety with thiocyanate under acidic conditions to form an amino acid thiohydantoin;

(c) cleaving the amino acid thiohydantoin from the polypeptide; and (d) identifying the cleaved amino acid thiohydantoin thereby identifying the C-terminal amino acid of the polypeptide.

14. The method of claim 13 wherein said polypeptide includes a side-chain carboxyl group, the method further comprising the steps of:

treating said polypeptide with acetic anhydride under basic conditions to form a mixed anhydride between the side-chain carboxyl group and the acetic anhydride; and treating the mixed anhydride with piperidine thiocyanate under non-acidic conditions to form a piperidine amide.

15. The method of claim 13 wherein said polypeptide includes a side-chain hydroxyl group, the method further comprising the step of acetylating the side-chain hydroxyl group.

16. The method of claim 13 wherein said step of cleaving includes alkylating said amino acid thiohydantoin.

17. The method of claim 13 wherein said anhydride is acetic anhydride and said basic conditions are maintained with an organic base having a $K_b$ in the range of between about $10^{-7}$ to about $10^{-12}$.

18. The method of claim 17 wherein said organic base is lutidine.

\* \* \* \* \*